(12) United States Patent
Irie et al.

(10) Patent No.: US 6,387,235 B1
(45) Date of Patent: May 14, 2002

(54) APPARATUS FOR THE SEPARATION AND FRACTIONATION OF DIFFERENTIALLY EXPRESSED GENE FRAGMENTS

(75) Inventors: Takashi Irie, Musashi-murayama; Hideki Hasegawa, Tachikawa; Hideki Kambara, Hachioji; Ken Ninomiya, Higashi-matsuyama, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/385,420

(22) Filed: Aug. 30, 1999

(30) Foreign Application Priority Data

Sep. 9, 1998 (JP) .......................................... 10-254845

(51) Int. Cl.[7] .............................................. G01N 27/26
(52) U.S. Cl. ...................................... 204/601; 603/604
(58) Field of Search ................................ 204/450, 451, 204/453, 600, 601, 604, 452, 603

(56) References Cited

U.S. PATENT DOCUMENTS

| 5,541,420 A | | 7/1996 | Kambara |
| 5,759,374 A | | 6/1998 | Takahashi et al. |
| 5,938,905 A | * | 8/1999 | Clegg et al. ................. 204/455 |
| 6,027,627 A | * | 2/2000 | Li et al. ...................... 204/603 |
| 6,132,582 A | * | 10/2000 | King et al. .................. 204/604 |

FOREIGN PATENT DOCUMENTS

| JP | 6-138037 | | 5/1994 |
| JP | 406174693 A | * | 6/1994 |
| JP | 7-181164 | | 7/1995 |
| JP | 9-127058 | | 5/1997 |
| JP | 9-288088 | | 11/1997 |

OTHER PUBLICATIONS

*The Newest Gas Chromatography Basic* (*I*), edited by Funasaka and Ikegawa, Published by Hirokawa, pp. 36–46 (1983.
Ito et al., "Fluorescent differential display: arbitrarily primed RT–PCR fingerprinting on an automated DNA sequencer", *FEBS Letters* 351 (1994) 231–236, Month Unknown.
Matz et al., "Ordered differential display: a simple method for systemic comparison of gene expression profiles", *Nucleic Acids Research*, 1997, vol. 25, No. 12 2541–2542.
Vos et al., "AFLP: a new technique for DNA fingerprinting", *Nucleic Acids Research*, 1995, vol. 23, No. 21, pp. 4407–4414, Date Unknown.
Derwent abstract of Kanbara et al. (JP406174693A).*

* cited by examiner

*Primary Examiner*—T. Tung
*Assistant Examiner*—Alex Noguerola
(74) *Attorney, Agent, or Firm*—Antonelli, Terry, Stout & Kraus, LLP

(57) ABSTRACT

An apparatus for the separation and fractionation of differentially expressed gene fragments includes a separating means including a capillary filled with a separation medium to separate DNA fragments by electrophoresis, a sampling means including sampling vessels to fractionate and sample the separated DNA fragments, according to their size, a transferring means to transfer buffer solution containing the separated DNA fragments to the sampling means, and a control means to control the sampling means based on a signal gained by detecting means, wherein a voltage for the electrophoresis and a length of the capillary are adjusted such that a spread in time of the separated DNA fragments caused by the transferring means during the transfer of the separated DNA fragments to the sampling vessels is smaller than a difference in separation time of the DNA fragments in the separating means.

25 Claims, 16 Drawing Sheets

TIMING WHEN THE PEAK TO BE COLLECTED IS FOUND

MIGRATION TIME

APPARATUS FOR THE SEPARATION AND FRACTIONATION OF DIFFERENTIALLY EXPRESSED GENE FRAGMENTS

BACKGROUND OF THE INVENTION

The present invention relates to an apparatus for the separation and fractionation of differentially expressed gene fragments. It relates more particularly to an apparatus and a process for the separation and fractionation of differentially expressed gene fragments (DNA fragments), which are suitable for searching a differentially expressed gene specific to a disease or a function.

Progress in life science and biotechnology has increased the need for the separation and fractionation of the DNA fragments. In particular, in progress in human genome and other genome projects, intensive attempts have been made to analyze the whole of expressed genes in an individual, to extract a differentially expressed gene specific to a certain organ or a gene involved with a specific function or disease, and to analyze the functions of the extracted gene. Accordingly, demands have been made to provide an apparatus which can analyze the whole of a multitude of samples and separate and sample differentially expressed gene (DNA) fragments with efficiency.

Of processes for detecting expression patterns of genes, some processes are based upon the size analysis of DNAs using electrophoresis. Such processes include, for example, the differential display method (hereinafter briefly referred to as "DD method") (Nucleic Acids Research, Vol. 25, No. 12, pp.2541–2542(1997)), the fluorescence differential display method (hereinafter simply referred to as "FDD method") (FEBS Lett., 351(2), 231–236, September 1994), the amplified fragments length polymorphism method (hereinafter simply referred to as "AFLP method") (Nucleic Acids Research, Vol. 23, No. 21, pp. 4407–4414(1995)).

To be more specific, according to these methods, mRNAs are extracted from different biological tissues (e.g., from a normal cell and a cancerous cell), translated to cDNAs through reverse transcription, the resulting cDNAs are fragmented with a restriction enzyme treatment, the resulting fragments are then subjected to amplification by polymerase chain reaction (PCR) using an arbitrary primer (according to the DD method or FDD method) or a selected primer (according to the AFLP method), and the obtained PCR products are electrophoresed for the size separation to compare the obtained electropherograms. By way of illustration, if there is a DNA fragment which is specifically strongly observed in the cancerous cell, the DNA fragment is a candidate for a differentially expressed gene specific to the cancer, and is separated and sampled. According to a conventional procedure, the size separation of DNAs by electrophoresis, and the separation and fractionation of a differentially expressed gene are conducted in the following manner.

By way of illustration, when a slab gel about 0.3 mm thick is used as a separation medium, a mixture (a base length marker) of DNA fragments each having a known length is electrophoresed in some electrophoresis lanes, and a sample DNA to be analyzed, which has been labeled with a fluorophore, is electrophoresed in the other electrophoresis lanes. In general, if base lengths are analyzed using a slab gel, the total amount of the sample DNA is approximately 1 pmol (picomole; $10^{-12}$ mole), and the volume of the sample DNA solution is several microliters ($\mu$L), each supplied to one electrophoresis lane. The sample is supplied to wells formed at an end of the slab gel, and then a voltage is applied to electrophorese the sample DNA.

After completion of the electrophoresis, an image formed on the gel is read out by an image reader. Such an image reader generally employs a technique of scanning laser light upon the gel surface and imaging the obtained fluorescent intensities to read out the positions of DNA bands in the slab gel.

In the electrophoresis on a slab gel, electrophoresis lanes often bend due to the effect of a distribution of temperature in the gel surface or the like to cause distortions in image. These distortions in image are corrected or calibrated in actual analysis and a base length pattern of the sample DNA is determined by a comparison between the positions of bands of the marker and those of the sample DNA. If a differential band is detected based on the comparison among base length patterns of different samples, the band is cut out from the gel to separate and collect the DNA fragment. The cut-out piece of gel is immersed in a buffer solution, allowed to stand for several hours or overnight to elute the DNA fragment from the gel into the buffer solution. The eluted DNA fragment is purified and then subjected to a sequencing reaction.

The conventional procedure requires a minute and precise technique to cut out a differential band in a precise size from the gel and thus requires a skilled and experienced person to handle. In addition, the extraction and purification of the DNA fragment from the cut-out gel require labor and a long period of time.

The gene expression profiling requires to analyze large amounts of samples, since comparisons between individual organs, between a normal tissue and a disease (e.g., cancer) tissue, or between a parent and a child, for example, are carried out using a combination of several tens of primers. Strong demands have therefore been made to improve working efficiency.

As examples of automatic apparatus for the separation and fractionation of differentially expressed gene fragments (DNA fragments), there may be mentioned one described in Japanese Patent Laid-open No. 7-181164 (hereinafter referred to as "the first conventional technique"), in which sample DNAs are electrophoresed using capillaries or slab gels each filled with a separation medium, and DNA fragments eluted into sheath flows of a buffer solution, transferred with the flow of the buffer solution by a transfer tube and sampled to sampling vessels. In this apparatus, the vessels are actuated according to detection signals of the DNA fragments eluted into sheath flows to collect a target DNA fragment automatically.

Separately, an apparatus is described in Japanese patent Laid-open No. 6-138037 (hereinafter referred to as "the second conventional technique"), in which first capillaries and second capillaries are respectively disposed in an optical cell face to face at specified gaps, which optical cell serves to detect DNAs labeled with fluorophores, and the DNA fragments eluted from the first capillaries into the optical cell are transferred to the second capillaries. In this apparatus, inner diameters of the second capillaries are greater than those of the first capillaries to introduce the DNA fragments to the second capillaries with ease and reliability.

SUMMARY OF THE INVENTION

Japanese Patent Laid-open No. 7-181164 (the first conventional technique) discloses fundamental constitutive elements of the apparatus, but fails to disclose a practical structure of the transfer tube, a concrete flow rate of the buffer solution and other parameters in a practical manner, which parameters are essential features for determining the performances of separation and fractionation of DNA fragments (in particular precision in separation of the DNA fragments, and required time to collect the DNA fragments). Japanese Patent Laid-open No. 6-138037 (the second conventional technique) lacks descriptions regarding the separation and fractionation of DNA fragments.

Accordingly, it is an object of the invention to improve the apparatus disclosed in Japanese Patent Laid-open No. 7-181164 (the first conventional technique) and thus to provide an apparatus for the separation and fractionation of differentially expressed gene fragments, which can shorten a required time for the separation and fractionation of DNA fragments and provide high separation.

The present inventors reviewed in detail the apparatus (fraction collector) disclosed in Japanese Patent Laid-open No. 7-181164 (the first conventional technique), and found that the performances of the separation and fractionation are significantly affected by a process for transferring DNA fragments through a transfer tube. To be more specific, the flow of a buffer solution in a transfer tube becomes a Poiseuille flow due to the viscosity of the buffer solution, and it is slower in the vicinity of a tube wall than at the center of the transfer tube, and has a flow rate distribution in a cross section perpendicular to the tube axis of transfer tube. As DNA fragments have small diffusion coefficients due to their large molecular weights, they are significantly affected by the distribution in flow rate (differences in flow rate) of buffer solution when they are uniformly injected with respect to the cross section perpendicular to the tube axis of transfer tube, and DNA bands separated by the gel and eluted into the buffer solution are spread out in time. DNA fragments (of base lengths of several tens to hundred) typically have a diffusion coefficient D of $10^{-5}$ mm$^2$/sec.

Defining an inner diameter of the transfer tube as r and an average flow rate of the buffer solution flowing through the transfer tube as u, a spread Δtp in time of DNA fragments in the transfer tube can be determined with reference to the formula (formula (1)) of Goley (edited by Funasaka and Ikegawa, "Contemporary Gas Chromatography (I), Fundamentals" pp. 36–46, Hirokawa Shoten, Japan). This formula represents a theoretical plate height, H, as an index of the efficiency of a separation column and is known in the theoretical fields of gas chromatograph and liquid chromatograph.

$$H=2D/u+(1+6k+11k^2)r^2u/\{24D(1+k)^2\} \quad (1)$$

where r is an inner diameter of a transfer tube (a capillary), u is an average flow rate of a fluid (a buffer solution) in the transfer tube (capillary) and k is a distribution coefficient.

In the formula of Goley (the formula (1)), when the flow is assumed to be a simple flow in the tube, the distribution coefficient is set to k=0, and the formula 1 is rendered to be the following formula (2). Defining a standard deviation of spatial spread of DNA fragments eluted to the buffer solution in the longitudinal direction of the transfer tube as σ and a length of the transfer tube as L, the parameter H is defined by the following the formula (3):

$$H=(2D/u+r^2u/(24D) \quad (2)$$

$$H=\sigma^2/L \quad (3)$$

As the diffusion coefficient D of DNA fragments is small, the first term of the formula (2) can be neglected. The spread Δtp in time which is calculated according to the formulae (2) and (3) is, therefore, approximated to the following formula (4). To be more specific, when DNA fragments each having a distribution width of δ function are injected to an inlet of the transfer tube in a uniform manner, the width of spatial spread of the DNA fragments in the longitudinal direction of the transfer tube is expressed as σ, and Δtp is expressed by the formula (4).

$$\Delta tp=\sigma/u=r\sqrt{\{L/(24uD)\}} \quad (4)$$

The results of an experiment with varying L demonstrate that Δtp was proportional to √(L) in the formula (4) and the results of an experiment with varying u demonstrate that Δtp was proportional to √(u$^{-1}$) when DNA fragments were uniformly injected with respect to the cross section perpendicular to the tube axis of transfer tube. Thus, it has been confirmed by experiments that the formula (4) holds well.

The above results demonstrate that the length of transfer tube L is to be shorten, the inner diameter of transfer tube r is to be lessen and the flow rate of buffer solution in the transfer tube is to be increased in order to minimize the spread of bands in the transfer tube. These parameters have, however, limitations in practice. By ascertaining the practical limitations and employing optimum values for the parameters, an apparatus for the separation and fractionation of differentially expressed gene fragments can be provided, which apparatus provides minimized period of time required for the separation and fractionation and improved separation. To reduce the influence of Poiseuille flow, a sampling means for sampling DNA fragments alone which are transferred in the vicinity of the center of the transfer tube or a transferring means of using air flow containing the DNA fragments in the form of droplets can be employed, resulting in minimized spread in time of DNA fragments.

A difference in migration time between the detection of a DNA fragment and that of another adjacent DNA fragment both having different sizes is determined by the length of a capillary as a separation medium, and the migration voltage. By setting the spread in time of bands of DNA fragments caused by a transferring means to be smaller than the difference in migration time of the fragments, a target DNA fragment can be separated and collected.

According to a capillary electrophoresis separator where DNA fragments are separated using a capillary filled with a separation medium, as the capillary has satisfactory heat radiation characteristics, electrophoresis at high voltage can be achieved and hence size analyses at a higher rate can be achieved than an apparatus using a slab gel. By adding a separation and fractionation mechanism to such a capillary electrophoresis separator to make full use of the above characteristics, DNA fragments can be separated and fractionated in a simple manner at a high rate. In contrast to a slab gel, such a capillary requires only trace amount of a prepared sample (in general, approximately 10 nL (nanoliters)) to be injected into the capillary. Separate injection of a sample and a marker into the capillary prevents the prepared sample from contamination. The prepared samples can therefore be used for different multiple applications or objectives, resulting in reduced costs for preparation of samples on the whole of analysis.

Accordingly, the present invention provides, in an aspect, an apparatus for the separation and fractionation of differentially expressed gene fragments, which apparatus includes a separating means including one or a plurality of capillaries each filled with a separation medium to separate DNA fragments by electrophoresis, the DNA fragments each labeled with a fluorophore, a detecting means to apply laser light to the DNA fragments separated by the capillaries and to detect fluorescence emitted from the fluorophore, a transferring means including sampling tubes which are placed with their first ends opposed to the terminal ends of the electrophoresis capillaries at a specified gap, the separated DNA fragments being transferred to the openings of the first ends, a means to form sheath flows of a buffer solution and to carry the separated DNA fragments eluted from each capillary to the openings of the first ends by sheath flows of the buffer solution, a sampling means including sampling vessels to fractionate and sample the DNA fragments according to their sizes, the DNA fragments transferred by the sampling tubes, and a control means to control the sampling means based on a signal gained by the detecting means. The apparatus has the following features:

(1) The sampling tubes each have a length ranging from 5 cm to 15 cm and an inner diameter ranging from 50 $\mu$m to 100 $\mu$m and the buffer solution flowing through the sampling tubes each have a flow rate of approximately 10 mm/sec.

(2) The apparatus may have a means to form droplets of the buffer solution containing the DNA fragments at the second ends of the sampling tubes, the DNA fragments transferred by the sampling tubes, and a transporting means to transport the formed droplets by airflow to the sampling vessels.

(3) The apparatus may further include a reservoir placed with second ends of the sampling tubes to contain the buffer solution eluted from the second ends, the reservoir having apertures at its bottom, and the apertures each having such a diameter that each sampling tube can be placed therethrough, a first tube to transport a washing fluid to the reservoir, and a second tube to drain the buffer solution from the reservoir, in which the second ends of the sampling tubes penetrate the apertures to transport the DNA fragments transferred by the sampling tubes to the sampling vessels.

(4) The laser light may be applied to the gap or to the capillaries.

(5) The apparatus may include a plurality of the capillaries in the separating means, and a voltage applying means to apply a voltage for electrophoresis to each of the capillaries independently.

(6) The apparatus may have a plurality of the capillaries in the separating means, and a voltage applying means to apply a voltage for electrophoresis to each of the capillaries independently, in which the voltage applying means changes the voltage during electrophoresis based on the signal gained by the detecting means.

(7) The sampling tubes may each have a length ranging from 5 cm to 15 cm and an inner diameter approximately ten times greater than the outer diameter of each capillary, and the buffer solution flowing through the sampling tubes may have a flow rate ranging from 0.3 mm/sec to 1 mm/sec.

The invention provides, in another aspect, an apparatus for the separation and fractionation of differentially expressed gene fragments, which apparatus includes a separating means containing a capillary filled with a separation medium to separate DNA fragments by electrophoresis, the DNA fragments each labeled with a fluorophore, a detecting means to apply laser light to the DNA fragments separated by the capillary and to detect fluorescence emitted from the fluorophore, a first tray to hold wells for holding a sample solution containing the DNA fragments, a second holder to hold wells for holding a marker solution containing a marker, and an injecting means to inject the sample solution and marker solution into the capillary separately.

In a further aspect, the invention provides an apparatus for the separation and fractionation of differentially expressed gene fragments, which apparatus includes a separating means including a capillary filled with a separation medium to separate DNA fragments by electrophoresis, the DNA fragments each labeled with a fluorophore, a detecting means to apply laser light to the DNA fragments separated by the capillary and to detect fluorescence emitted from the fluorophore, a means to form a sheath flow of a buffer solution and to carry the separated DNA fragments eluted from the terminal end of electrophoresis capillary, a sampling means including sampling vessels to fractionate and collect the DNA fragments according to their sizes, a transferring means to transfer the buffer solution containing the DNA fragments to the sampling means, and a control means to control the sampling means based on a signal gained by the detecting means, in which a spread in time of the DNA fragments caused by the transferring means during transfer of the DNA fragments to the sampling vessels is smaller than differences in separation times of the DNA fragments in the separating means, and wherein the transferring means includes a sampling tube which is placed with its end opposed to the terminal end of the electrophoresis capillary at a specified gap, and the separated DNA fragments are transferred to the openings of the first end.

The present invention provides, in yet another aspect, a process for the separation and fractionation of differentially expressed gene fragments, which process includes: a step for injecting a sample DNA solution, and a marker solution into a capillary separately, the sample DNA solution containing DNA fragments each labeled with a fluorophore, the marker solution containing a marker labeled with another fluorophore different from the aforementioned fluorophore with which the DNA fragments are labeled, and the capillary filled with a separation medium, a step for separating the DNA fragments and the marker by electrophoresis, and a step for applying laser light to the DNA fragments and marker separated by the capillary and detecting fluorescence emitted from different species of fluorophores to obtain an electropherogram of the sample DNA.

The invention provides, in a further aspect, a process for the separation and fractionation of differentially expressed gene fragments, which process includes: a step for injecting each of plural sample DNA solutions and a marker solution separately into each of plural capillaries, the DNA solutions containing DNA fragments each labeled with a fluorophore, the marker solution containing a marker labeled with another fluorophore different from the aforementioned fluorophore with which the DNA fragments are labeled, and the capillaries each filled with a separation medium, a step for separating the DNA fragments and the marker by electrophoresis, a step for applying laser light to the DNA fragments and marker separated by each capillary and detecting the fluorescence emitted from different species of fluorophores to obtain electropherograms of the individual sample DNAs and to select a target DNA fragment to be collected based on the electropherograms, a step for separating a sample DNA solution by electrophoresis on a slab gel, the sample DNA solution containing the selected target DNA fragment, and a step for sampling a band of the selected DNA fragment from the slab gel, the DNA fragment separated by electrophoresis.

According to the invention, DNAs of differentially expressed genes can be separated and fractionated automatically with a satisfactory separation, resulting in increased efficiency of researches for pathogenic genes and genes differential to specific functions based upon the gene expression profiling.

An embodiment of the invention can be summarized as follows with reference to FIG. 1: The apparatus includes capillaries 10 to separate DNA fragments each labeled with a fluorophore, detecting means (4a, 6a, 6b, 4b and 2) to apply laser light 28 to the separated DNA fragments and to detect fluorescence emitted therefrom, sampling tubes 14 which are placed with their first ends opposed to the ends of the electrophoresis capillaries at a specified gap, the separated DNA fragments are transferred to the openings of the first ends, means 8 to form sheath flows of a buffer solution and to carry the separated DNA fragments eluted from each of the capillaries to the openings of the first ends by sheath flows of the buffer solution, sampling means 15 including sampling vessels to fractionate and sample the DNA fragments according to their sizes, the DNA fragments being transferred by the sampling tubes, and control means 9, 17 to control the sampling means 15 based on a fluorescence signal. In this embodiment, the sampling tubes each have a length ranging from 5 cm to 15 cm and an inner diameter ranging from 50 $\mu$m to 100 $\mu$m, and the buffer solution flowing through the sampling tubes each have a flow rate of approximately 10 mm/sec. According to the apparatus of the invention, gene fragments can be separated and fractionated in a short time in a high separation, resulting in increased efficiency of the separation and fractionation procedures of differentially expressed gene fragments.

BRIEF DESCRIPTION OF THE DRAWINGS

These and other features, objects, and advantages of the present invention will become apparent upon a consideration of the following description of the invention when read in conjunction with the drawings, in which.

DESCRIPTION OF THE PREFERRED EMBODIMENTS

Figure 1:
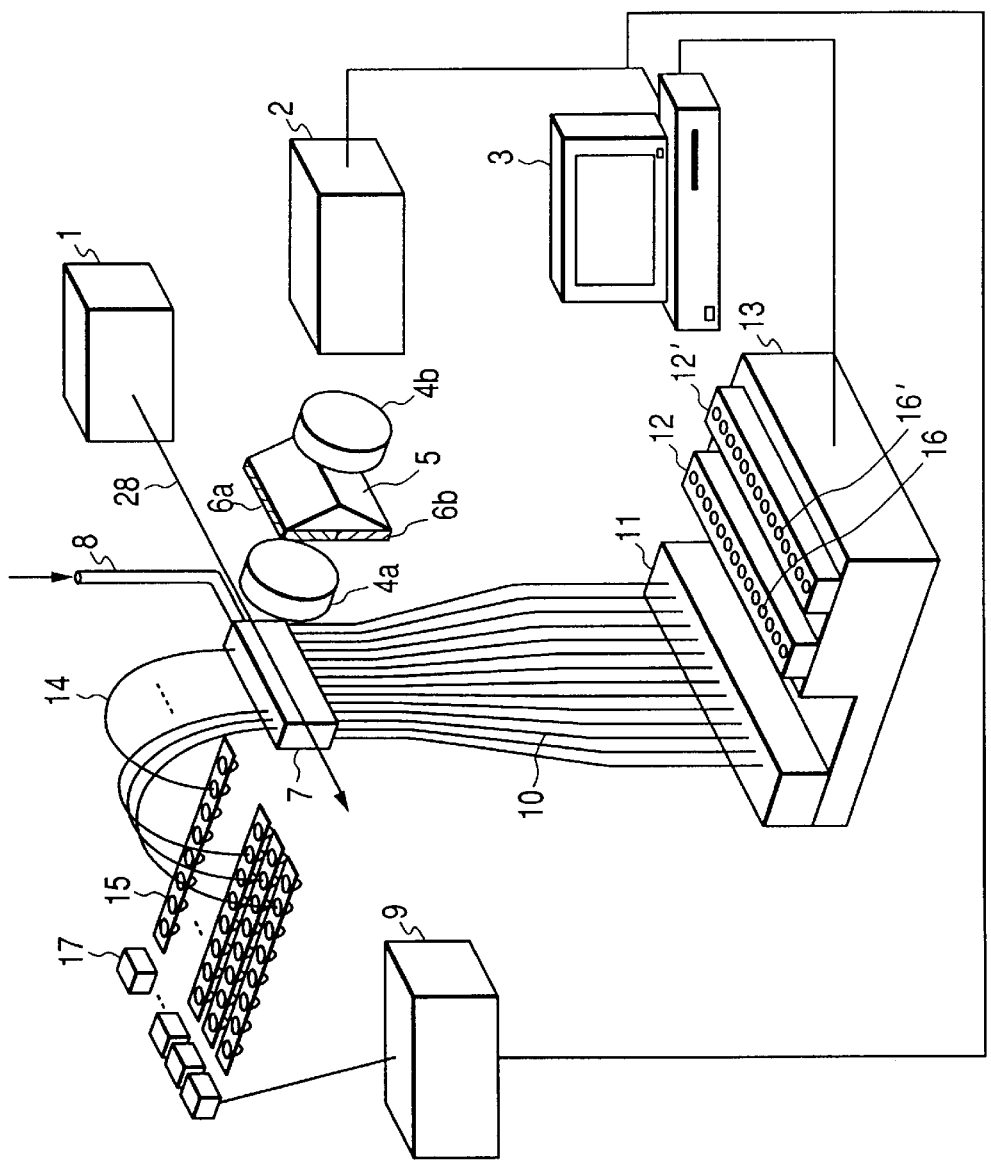
FIG. 1 is a diagram illustrating the configuration of an apparatus for the separation and fractionation according to a first embodiment of the present invention.

FIG. 1 is a diagram illustrating a configuration of the apparatus according to the first embodiment of the invention. A sample DNA to be analyzed has been labeled with a fluorophore in advance in a conventional manner. In the apparatus, sample tray 12 is placed which is formed with a plurality of wells 16 for holding sample solutions, the wells 16 are respectively corresponding to each of plural capillaries 10, and the capillaries 10 are each filled with a separation medium. The sample is injected into each capillary 10 from each well 16 corresponding to the capillary. As the separation medium, cross-linked polyacrylamide gel having a concentration of 4%, a degree of cross-linking of 5% and containing 7 molar concentration urea is used, for example. The separation medium is not limited to this, and any other separation media can be used according to parameters such as size of the sample DNA, required separation, and analysis time.

Figure 2:
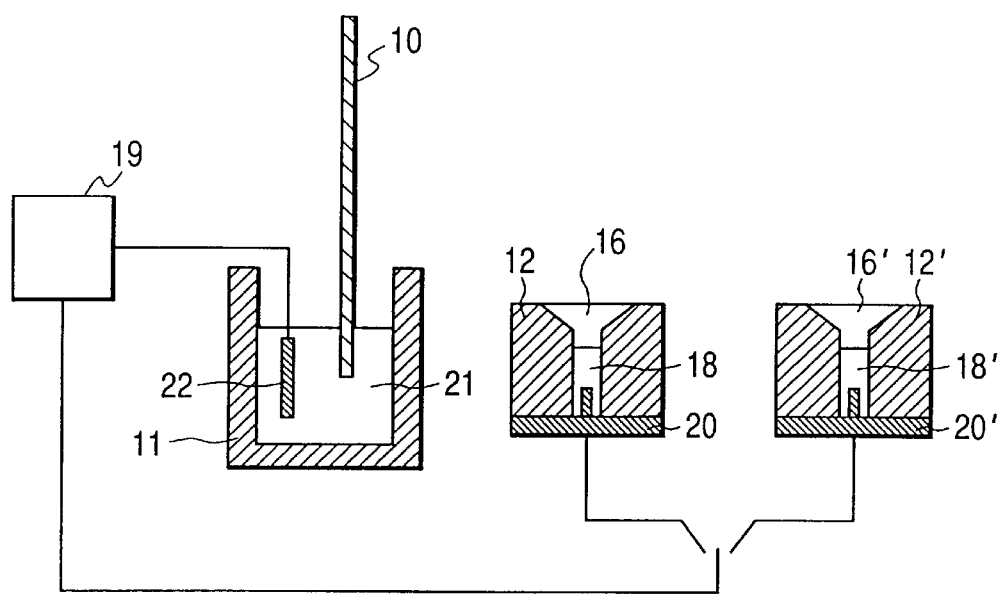
FIG. 2 is a cross sectional view illustrating the configuration of a sample injection unit of the apparatus according to the first embodiment of the present invention.

FIG. 2 is a cross sectional view illustrating the configuration of a sample injection unit of the apparatus. An injection end of the capillary 10 immersed in buffer 21 for electrophoresis in buffer reservoir 11, which buffer 21 is obtained by adding 7 molar concentration urea to a TBE (Tris-Borate-EDTA) buffer solution. When the sample DNA solution is injected, sample stage 13 (FIG. 1) is moved to immerse the injection end of the capillary 10 into sample DNA solution 18 in the well 16 for holding sample solution. At the bottom of the well 16 for holding sample solution is provided electrode 20. A voltage is applied for a short time (10 sec to 30 sec) between the electrode 20 and an electrode (not shown) arranged in the optical cell 7 (FIG. 1) with high voltage power supply 19 to inject the sample solution to the injection end of the capillary 10. After the injection of the sample solution, the injection end of the capillary 10 is returned to the buffer reservoir 11, and then a constant voltage (25 V to 300 V per 1 cm of capillary) is applied between the electrode 20 and the electrode placed in the optical cell 7 (FIG. 1) with the use of the high voltage power supply 19 to migrate DNA fragments in the capillary 10 by electrophoresis for size separation. The application of voltage, movement of the sample stage 13 (movements in the vertical and horizontal directions) are fully controlled by personal computer 3 (FIG. 1).

The DNA fragments are migrated through the capillary 10 from the injection end of the capillary toward the optical cell 7 in increasing size order, and eluted from the other end of the capillary 10 which is inserted and placed in the inside region of the optical cell 7. In the inside of the optical cell 7 is formed a sheath flow of the buffer solution in parallel with the axial direction of the capillary 10. The DNA fragments eluted from the other end of the capillary 10 are carried across the optical axis of laser light 28 to sampling tube 14, which laser light 28 is applied to the inside region of the optical cell 7. The end of the sampling tube 14 is placed opposed to the end of the capillary 10 in a coaxial manner at a specified gap. The configuration of the optical cell 7 will be described in detail later (FIGS. 5A, 5B, 6–8 and 10).

By applying the laser light 28 from laser light source 1 simultaneously to the gaps in the inside region of the optical cell 7, a plurality of DNA fragments each eluted from each end of a plurality of capillaries 10 can be measured simultaneously. The buffer solution to form sheath flows in the inside region of the optical cell 7 is obtained by adding 0.02% of a surfactant (Tween 20) to a TBE buffer solution for electrophoresis, in order to prevent the adsorption of DNA fragments. The buffer solution is supplied by gravity through inlet 8 of buffer solution into the inside region of the optical cell 7, and drained from the a plurality of sampling tubes 14. The DNA fragments are carried through the sheath flows into the sampling tubes 14, and the DNA fragments transferred through the sampling tubes 14 are carried with the buffer solution into wells placed on the fraction collectors 15, each of which wells 16 corresponds to each sampling tube 14.

The fraction collectors 15 are provided as many as the capillaries 10. The movement of each of the fraction collectors is controlled by each of the actuators 17 of the fraction collectors. To sample a target DNA fragment to be collected, the movement of the fraction collectors 15 is controlled by detecting the fluorescence emitted from the fluorophore which labels DNA fragments, through lenses 4a, 4b, image-splitting prism 5, band-pass filters 6a, 6b by two-dimensional detector 2, analyzing the detection signal through the personal computer 3 to identify the target DNA fragment, and giving signals to controller 9. Individual actuators 17 are respectively controlled by signals gained by the controller 9.

Upon the gene expression profiling, comparisons in sizes of DNA fragments is required per one sample. According to the AFLP method where information on the termini sequence of DNA fragments has been obtained in advance, determination of the size of a DNA fragment may sometimes reveal in which gene the DNA fragment is located. It is, therefore, significantly important to compare the sizes (lengths) of DNA fragments contained in samples among a plurality of samples or to determine the absolute values of the sizes of the DNA fragments. However, migration times of individual capillaries may often vary with each other even if DNA fragments having the identical sizes are migrated, due to fluctuations in length and inner diameter of the capillaries, in characteristics of the separation medium filled in the capillaries, in amounts and/or compositions of the injected samples. To correct these fluctuations, an identical marker (marker DNA) is added to individual samples, and sizes of DNA fragments contained in the individual samples are analyzed by the comparison in migration time between the DNA fragments and the marker DNA.

The marker DNA and the sample DNA should be labeled with different fluorophores with each other. By way of illustration, the marker DNA is labeled with tetramethyl-rhodamine (TAMRA) (with a maximum emission wavelength of 585 nm) and the sample DNA is labeled with ROX (with a maximum emission wavelength of 605 nm). By irradiation with the laser light, a fluorescence image is formed at the location where the laser light is applied. The image is observed at constant time intervals, by the highly sensitive two-dimensional detector 2, such as a cooled CCD camera, using the band-pass filters 6a, 6b and the image-splitting prism 5 each having wavelength characteristics mated to distributions in fluorescence wavelength of the individual fluorophores. Thus, electropherograms (changes in fluorescent intensity with time) of each capillary and each fluorophore are determined. The lenses 4a, 4b serve to form a fluorescence image on an imaging plane of the two-dimensional detector 2. The collection and analysis of data, the movement of the wells for holding sample solutions, and application of voltage to the capillaries are controlled by the personal computer 3. After the completion of determination, calibration curves of the individual capillaries are prepared, representing the relation between the peak of the marker DNA and the known base lengths of the marker. By calibrating electropherograms of the sample DNA using the calibration curves in actual measurement, the distribution of base lengths of the sample DNA can be obtained.

Figure 3:
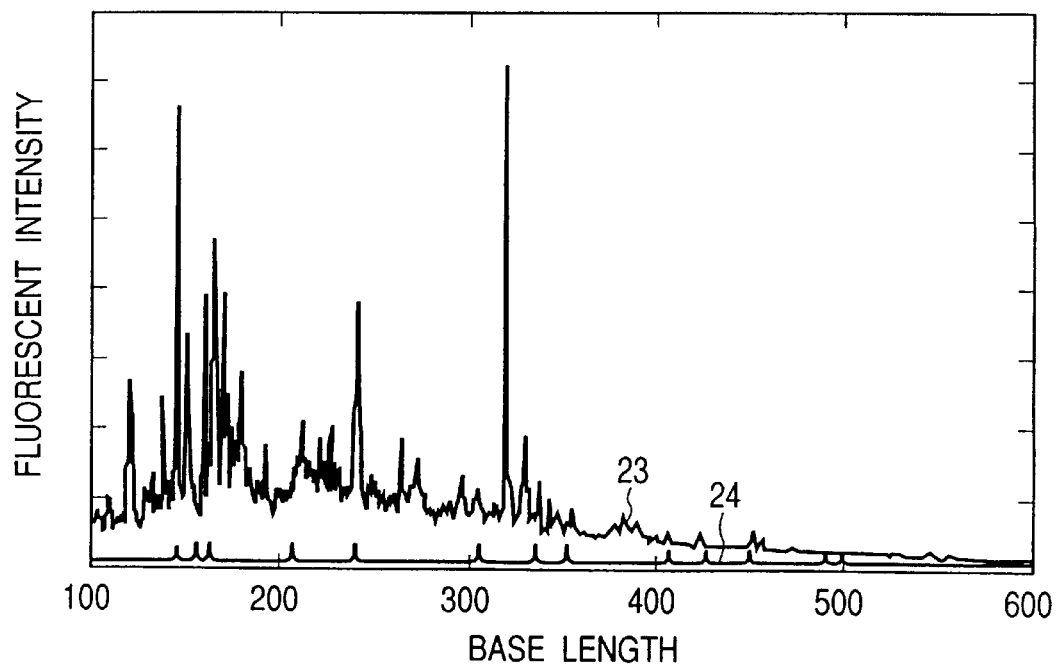
FIG. 3 is a diagram showing an illustrative electropherogram obtained with the use of the apparatus according to the first embodiment of the invention.

FIG. 3 is an illustrative electropherogram obtained using the instant apparatus, in which 23 is an electropherogram of a sample DNA and 24 is an electropherogram of a marker.

In the configuration of the apparatus shown in FIG. 1, the capillaries 10 and the sampling tubes 14 are separately arranged under and over the optical cell 7, whereas another configuration can be employed where the buffer reservoir 11, capillaries 10, sample tray 12 and sample stage 13 are arranged over the optical cell 7, and the sampling tubes 14 and fraction collectors 15 are placed under the optical cell 7 to form sheath flows in the direction from the top to the bottom of FIG. 1. It may also be possible that the fraction collectors 15 and the sample injection ends are arranged nearly in the same horizontal plane, with arranging the detecting system (lenses 4a, 4b, image-splitting prism 5, band-pass filters 6a, 6b and detector 2) over or under the horizontal plane.

Figure 4:
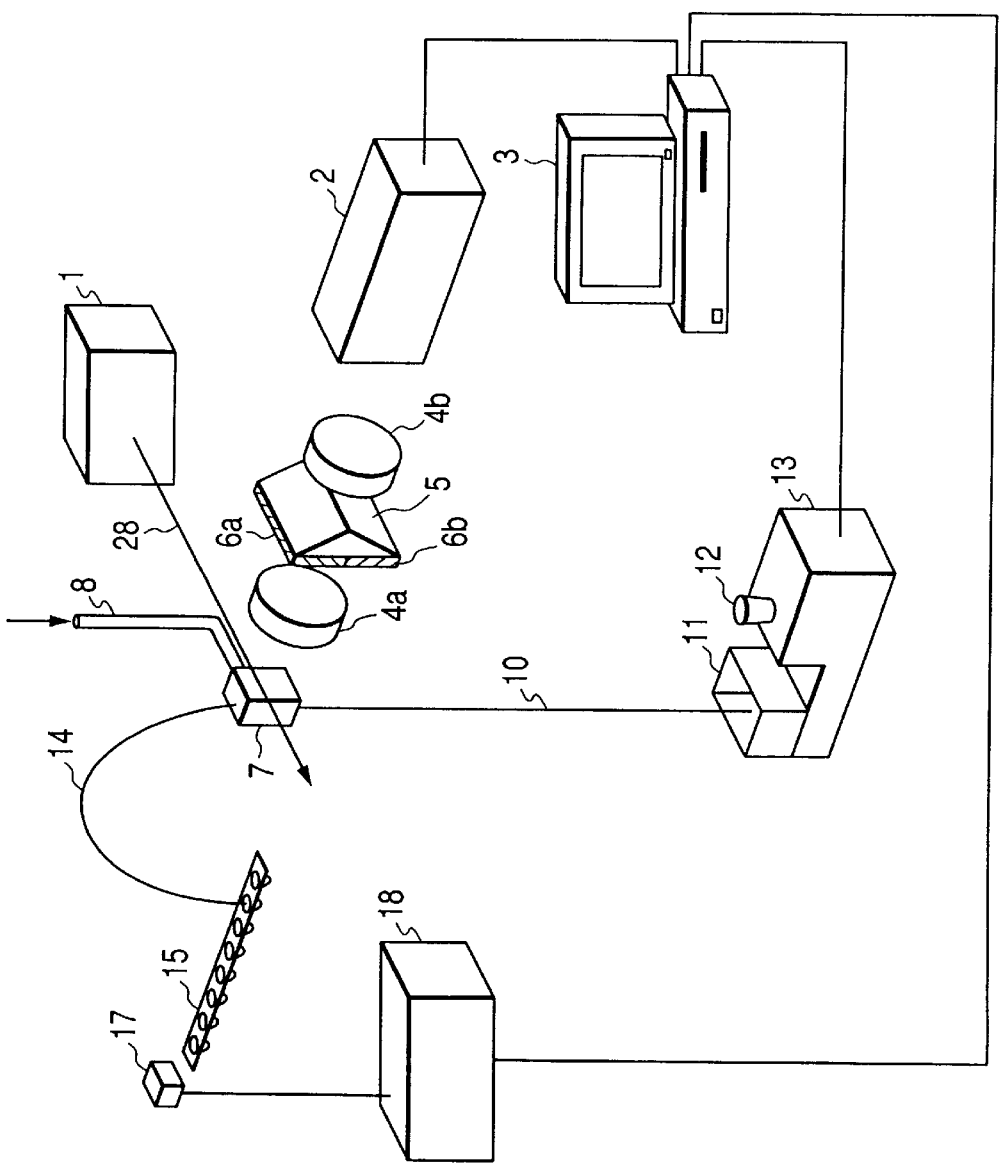
FIG. 4 is a diagram illustrating the configuration of an apparatus for the separation and fractionation according to a second embodiment of the present invention.

FIG. 4 is a diagram illustrating the configuration of the apparatus according to the second embodiment of the invention, which configuration is equivalent to that of the first embodiment shown in FIG. 1, except for using one capillary, one sample tray 12 for holding a well for holding the sample solution, and one fraction collector 15.

Individual units constituting the apparatus according to the first embodiment of the invention will now be described in detail.

Figure 5B:
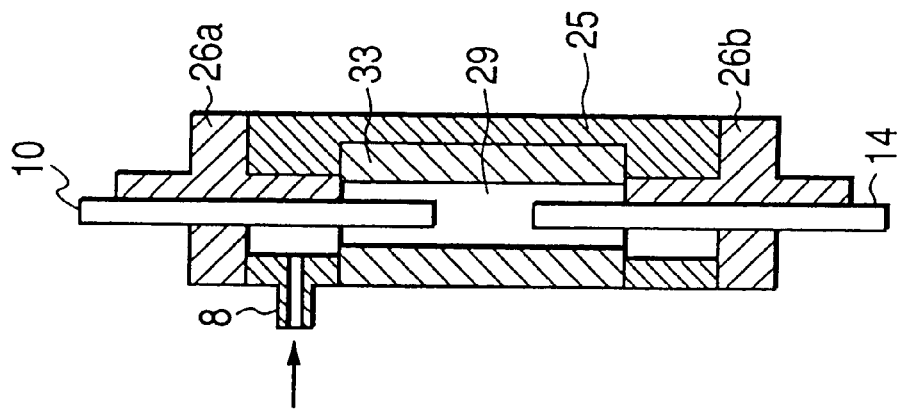
FIGS. 5A and 5B are diagrams showing the optical cell and a first illustrative configuration of transferring means of the apparatus according to the first embodiment of the present invention.
Figure 5A:
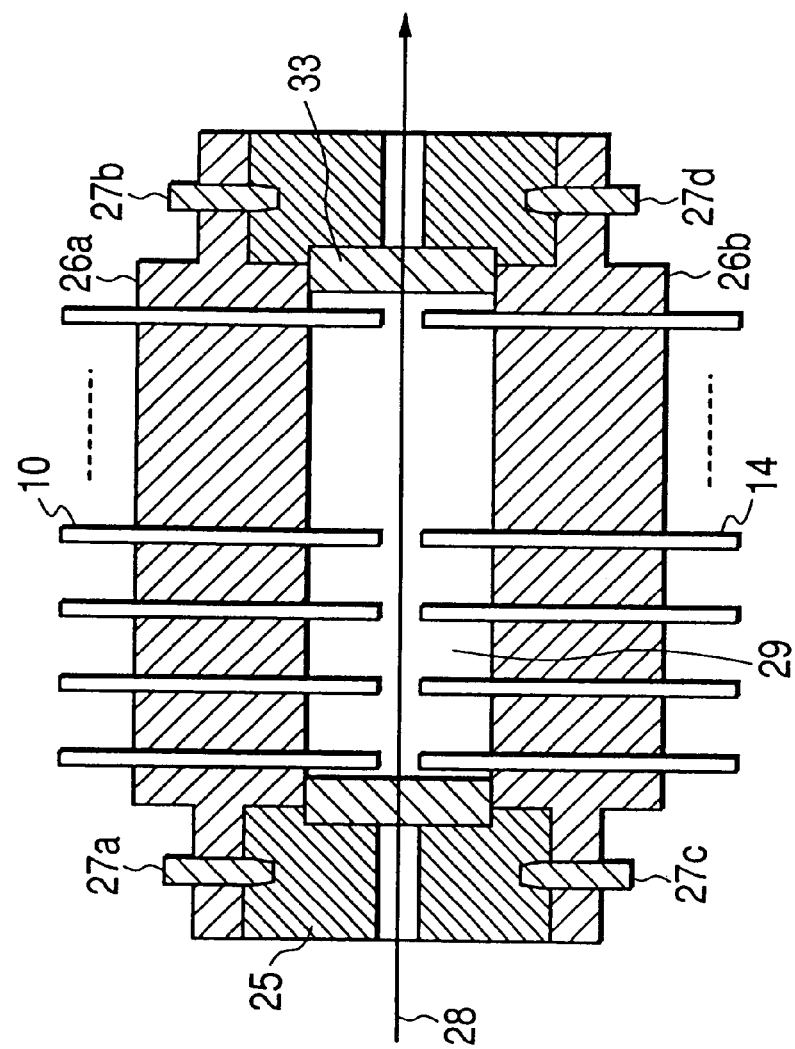

FIGS. 5A and 5B are diagrams respectively showing the optical cell and a first illustrative configuration of transferring means of the apparatus, where FIG. 5A is a cross sectional view of the optical cell and transferring means along with the direction of the optical axis of the laser light 28, and FIG. 5B is a cross sectional view of the same along with a direction perpendicular to the optical axis of the laser light 28.

Holder 25 of the optical cell holds optical cell 33 and supports holder 26a of the capillary and holder 26b of the sampling tube. Each of the capillaries 10 has an outer diameter of 200 μm and an inner diameter of 75 μm. The capillaries 10 are placed and fixed in parallel on the holder 26a, and the ends of the capillaries are then cut in a line. Each of the sampling tubes 14 has an outer diameter and an inner diameter of 200 μm and 75 μm, respectively, identical with those of the capillaries 10. The sampling tubes 14 are placed and fixed in parallel on the holder 26b, and the ends of the tubes are then cut in a line. The thus obtained array of capillaries and array of sampling tubes are placed face to face in coaxial manner at gaps of 1 mm inside the optical cell 33 made of quartz.

To ensure the application of the laser light 28 to the DNA fragments eluted from the capillaries 10 and to ensure the introduction of the eluted DNA fragments from each capillary 10 to corresponding each sampling tube 14, the inner width of the quartz optical cell 33 shown in FIG. 5B is rendered to be about several micrometers greater than the outer diameter of the capillary 10, and the capillary array and the sampling tube array are respectively inserted from over and under the cell into the inside region of the optical cell 33; and the positions of the holders 26a and 26b are adjusted by pins 27a, 27b, 27c, 27d for adjusting positions of the holders relative to the holder 25 of the optical cell. The buffer solution is introduced through the inlet 8 formed in the holder 25 of the optical cell into the optical cell and exhausted from a plurality of sampling tubes 14.

To increase the uniformity in flow rate distribution of the buffer solution in the optical cell 33 and thereby to ensure that the sheath flows have uniform flow rates at both ends of the capillary array, the apparatus has the following configuration (hereinafter referred to as "the configuration A"): Glass rods and 16 capillaries (i.e., 16 migration lanes) are aligned in an alternating sequence, which glass rods each have an outer diameter of 200 μm, identical with that of each capillary. In addition, another nine glass rods each are aligned in the outer sides at both ends of the capillaries. Separately, glass rods and 24 sampling tubes are arranged in an alternating sequence, and another one glass rod each is aligned in the outer sides at both ends of the sampling tubes. The interval between adjacent capillary (or sampling tube) and glass rod is 0.4 mm. In this procedure, the width of an array composed of a total of 49 capillaries and glass rods, and the width of an array composed of a total of 49 sampling tubes and glass rods are respectively 0.4×48=19.2 mm. The optical cell 33 has a width of 24 mm in the direction of the irradiation of the laser light. The ends of the capillaries 10 (or of the glass rods) are separated from the ends of the sampling tubes 14 (or of the glass rods) at gaps of 1 mm, and they are respectively inserted 3 mm into the inside region 29 of the optical cell 33 from its edge surface, which means the optical cell 33 has a height of 7 mm.

Key parameters in the above configuration include the length, inner diameter and outer diameter of each sampling tube, the flow rate of the buffer solution, the gap between the sampling tubes and capillaries, and the interval between adjacent aligned capillaries. Appropriate ranges of these parameters will now be described below.

The less the alignment gap of capillaries is, the more number of capillaries can be used simultaneously to detect DNA fragments. A conventionally available two-dimensional detector (e.g., a cooled CCD camera) has an effective area with a width of about 25 mm. If an optical system of equal magnification (1:1) is used, the optical cell should have a width (width in the direction of the irradiation of laser light) nearly equal to the width of the effective area, i.e., about 25 mm.

If capillaries having an outer diameter of 200 μm are aligned in a closest manner, the maximum number of capillaries which can be used simultaneously for the detection is 125. In practice, however, the precision in adjustment of the coaxes of the ends of capillaries and those of sampling tubes in the optical cell 33 may hardly be set to equal to or less than 0.1 mm, because of deformation of capillaries and sampling tubes. In actual procedures, when the optical cell has a configuration in which the capillaries and glass rods are aligned in an alternating sequence and the precision in adjustment of the ends of the capillaries and those of sampling tubes is set to equal to or less than 0.1 mm, the maximum number of capillaries which can be aligned is at most about 40, and in this case the interval between adjacent capillaries is 0.3 mm.

The gap length between ends of the capillaries and those of the sampling tubes may preferably range from 0.5 mm to 2 mm. If the gap is excessively small, part of the irradiated laser light scatters at terminal ends of the capillaries and sampling tubes due to irregularity of their cut surfaces, resulting in increased background in the detection of DNA fragments.

In addition, if the gap is less than about 0.5 mm, the DNA fragments have to be detected at a location in the vicinity of the inlet of sampling tube. At such a location in the vicinity of the inlet, the buffer solution has a higher flow rate and hence the resulting irradiation time of laser light to the DNA fragments is shortened to decrease the detection sensitivity of the DNA fragments. In contrast, if the gap is excessively large, the coaxial alignment of the ends of the capillaries and those of the sampling tubes cannot be adjusted with satisfactory precision, and DNA fragments might migrate into the adjacent sampling tube not corresponding to the present capillary due to spread of bands of the DNA fragments.

The insert lengths of the capillaries 10 and sampling tubes 14 into the inside region of the optical cell 33 are preferred to range from 3 mm to 5 mm. This insert length corresponds to a distance from the edge surface of the optical cell 33 to the terminal end of each capillary 10 and sampling tube 14, that is, to a length of a portion of each capillary 10 and sampling tube 14 which is exposed to the inside region 29 of the optical cell. In the vicinity of the inlet of buffer solution in the optical cell, the sectional area of the flow of the buffer solution varies comparatively, and a given entrance length is required for the flow of the buffer solution to form a complete laminar flow. If the insert length is excessively short, the uniformity of flow rates of the sheath flows is deteriorated, causing fluctuation in separation and detection sensitivity of the DNA fragments among the individual capillaries. If the insert length is excessively long, the capillaries may often deform due to their comparatively weak mechanical strength, along with the insertion into the optical cell. Consequently, the positions of ends of the capillaries and those of the sampling tubes can hardly be adjusted with satisfactory precision, resulting in deteriorated precision in adjustment of the positions. Accordingly, the optical cell 33 should preferably have a height, i.e. a total of the insert length and the gap mentioned above, ranging from about 6.5 mm to 12 mm.

The parameters of the inner diameter and length of the sampling tubes and the flow rate of the buffer solution (sheath flow) will now be reviewed in detail.

The spread in time, Δtp, of the DNA fragments flowing through the sampling tube varies according to the formula (1). To prevent the DNA fragment from spreading (i.e., deterioration of separation) during the transfer through the sampling tube, the length L of the sampling tube should be shortened, the inner diameter r of the sampling tube should be decreased and the flow rate u of the buffer solution should be increased. However, all these parameters have limitations in practice.

Increase of the flow rate u of the buffer solution inside the optical cell increases the flow rate of the buffer solution flowing through the sampling tube but deteriorates the detection sensitivity of the target DNA fragments.

In the configuration A using 16 capillaries and 24 sampling tubes, when the average flow rate of the buffer solution flowing through sampling tube is set to about 10 mm/sec, the flow rate of buffer solution in the optical cell is 0.21 mm/sec, with a detection sensitivity of DNA fragments of 0.01 fmol/μL (femtomole/microliter: $10^{-9}$ M (mol/L)). This detection sensitivity is sufficiently applicable to expression profiling of genes according to the DD method, the AFLP method or the like.

To shorten the length L of the sampling tube, the sizes of fraction collectors must be reduced. In consideration of the sizes of individual wells of fraction collectors and the configuration of actuating system thereof, individual fraction collectors corresponding to individual capillaries should be arranged at intervals of at least 3 mm to 5 mm. When the width of the optical cell 33 is about 25 mm, the interval of arranged sampling tubes in the configuration A preferably ranges from 0.6 mm to 0.8 mm in order to bring each capillary 10 in correspondence with each sampling tube 14 and to prevent the DNA fragments eluted from one capillary from migrating into another adjacent sampling tube not corresponding to the capillary. When one to five capillaries are used, the total width of the sampling tube array is to range from 0 mm to 3.2 mm. In this case, the total width required for the array of fraction collectors is to range from 3 mm to 20 mm, and therefore a sampling tube having a length of equal to or more than about 50 mm can be connected to a fraction collector.

However, if a greater number of capillaries, for example 16 capillaries, are used, the total width for an array of the whole fraction collectors should range from 45 mm to 60 mm, which requires sampling tubes each having a length ranging from 50 mm to 100 mm. In the configuration A, the maximum number of the capillaries 10 to be used is about 40, and in this case the total width required for an array of the whole fraction collectors is to range from 120 mm to 150 mm, which requires sampling tubes each having a length ranging from 100 mm to 150 mm.

As pressure loss in the sampling tube increases with a decreasing inner diameter r of the tube, the pressure must be increased to obtain a desired flow rate of the buffer solution. Such a pressure loss is in general proportional to an inner diameter of a tube involved to the fourth power. A pressure practically formed by gravity is at most about 0.1 atm (with a drop of 1 m), and a pressure more than this invites upsizing of the apparatus on the whole.

A mechanical pump for transferring may be used to increase the flow rate of buffer solution, but instability of the flow would slightly generate with the use of such a mechanical pump and may cause fluctuation in strength of the tube. When a sampling tube of 75 μm diameter and 10 cm length is used, a flow rate of buffer solution flowing through the sampling tube of 10 mm/sec is obtained at a drop equal to or less than 0.5 mm. In this test, the spread in time Δtp of the DNA fragments flowing through the sampling tube is about 10 sec in terms of half band width. In the actual sampling, parameters for migration such as the applied voltage and the lengths of the capillaries should be adjusted in such a manner that the time just mentioned above (about 10 sec) is shorter than a time interval with which a target DNA fragment is detected separately from other DNA fragments by electrophoresis. This time interval corresponds to a time lag between the time when the target DNA fragment is detected and the time when another DNA fragment is detected.

Figure 6:
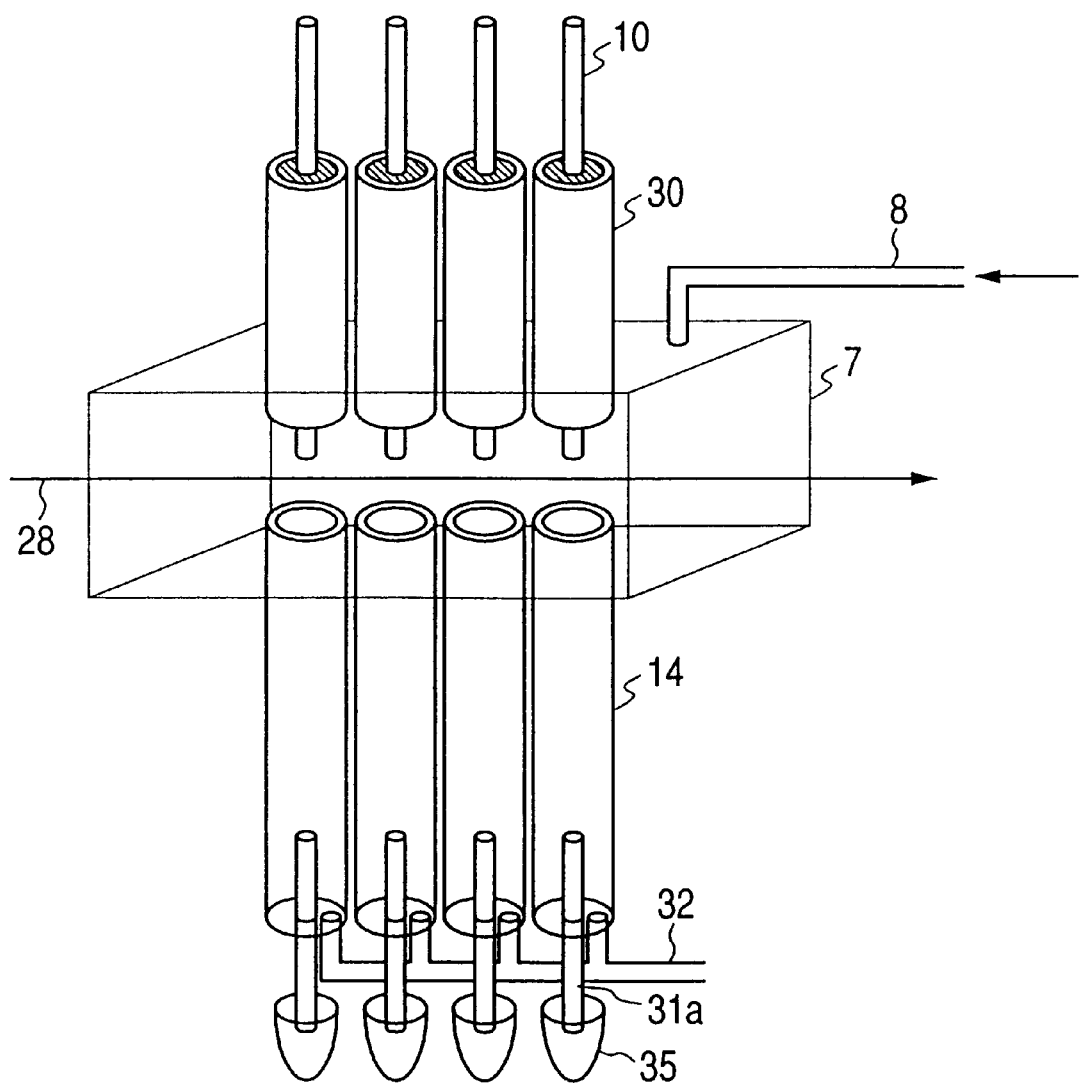
FIG. 6 is a diagram showing the optical cell and a second illustrative configuration of transferring means of the apparatus according to the first embodiment of the present invention.

FIG. 6 is a perspective view showing the optical cell and a second illustrative configuration of transferring means of the apparatus. In this connection, the optical cell 7 illustrated in FIGS. 6, 7, 8 and 10 is schematically illustrated, having a configuration in which the optical cell 33, its holder 25, and the holders 26a, 26b of the capillaries and the sampling tubes as illustrated in FIGS. 5A and 5B are integrated. The optical cell 7 shown in FIG. 6 has a configuration in which the sampling tubes 14 each have an inner diameter greater than the outer diameter of the capillaries. The center of the ends of each capillary 10 is so arranged as to mate the center of inlet side of a corresponding sampling tube 14 with the use of tube 30 for supporting and adjusting the position of the capillary, which tube has an identical diameter with that of the sampling tube. To sample a DNA fragment alone which is flowing in the vicinity of the center of the sampling tube 14 to the sampling vessel 35 placed on the fraction collector, additional tube 31a of the sampling tube 14 is arranged in the center of the inside region around the outlet of the sampling tube 14. The additional tube 31a has an inner diameter of 75 μm. The buffer solutions flowing through individual sampling tubes are drained via drain tube 32. According to the above mentioned configuration, the DNA fragments flow in the vicinity of the center of each sampling tube, preventing the sampling of the DNA fragments from affected by decrease in flow rate of the buffer solution in the vicinity of tube wall due to Poiseuille flow. As DNA molecules have small diffusion coefficients, DNA fragments flowing in the vicinity of the center of the sampling tube remain in the vicinity of center.

In the illustrative configuration shown in FIG. 6, the sampling tube 14 has an inner diameter of 2 mm and an outer diameter of 3 mm, and the capillary 10 has an inner diameter of about 75 μm and an outer diameter of 200 μm. The flow rate of the buffer solution flowing through the sampling tube should preferably be minimized within the range not affected by heat convection due to temperature distribution inside the sampling tube, and it is set to 0.3 mm/sec in this illustrative configuration. Under these conditions, the flow volume of the buffer solution flowing through each sampling tube is about 1 μL/sec. When the size (width in the direction of the irradiation of laser light) of the optical cell is set to 25 mm as in the configuration shown in FIGS. 5A and 5B, the maximum number of sampling tubes 3 mm in outer diameter is eight even if they are arranged in a closest manner. The configuration shown in FIG. 6 cannot be applied to a case where nine or more capillaries are used. If eight sampling tubes are employed, the flow rate of the buffer solution in the optical cell is 0.1 mm/sec, with which a satisfactory detection sensitivity can be obtained. In this case, a sufficient detection sensitivity can be obtained even when the flow rate in the optical cell is increased to about 1 mm/sec. The lengths of the sampling tubes should preferably minimized as in the configuration shown in FIG. 6, and the width of the fraction collector per one capillary is set to 5 mm and the lengths of the sampling tubes are set to 5 cm, for instance.

Figure 7:
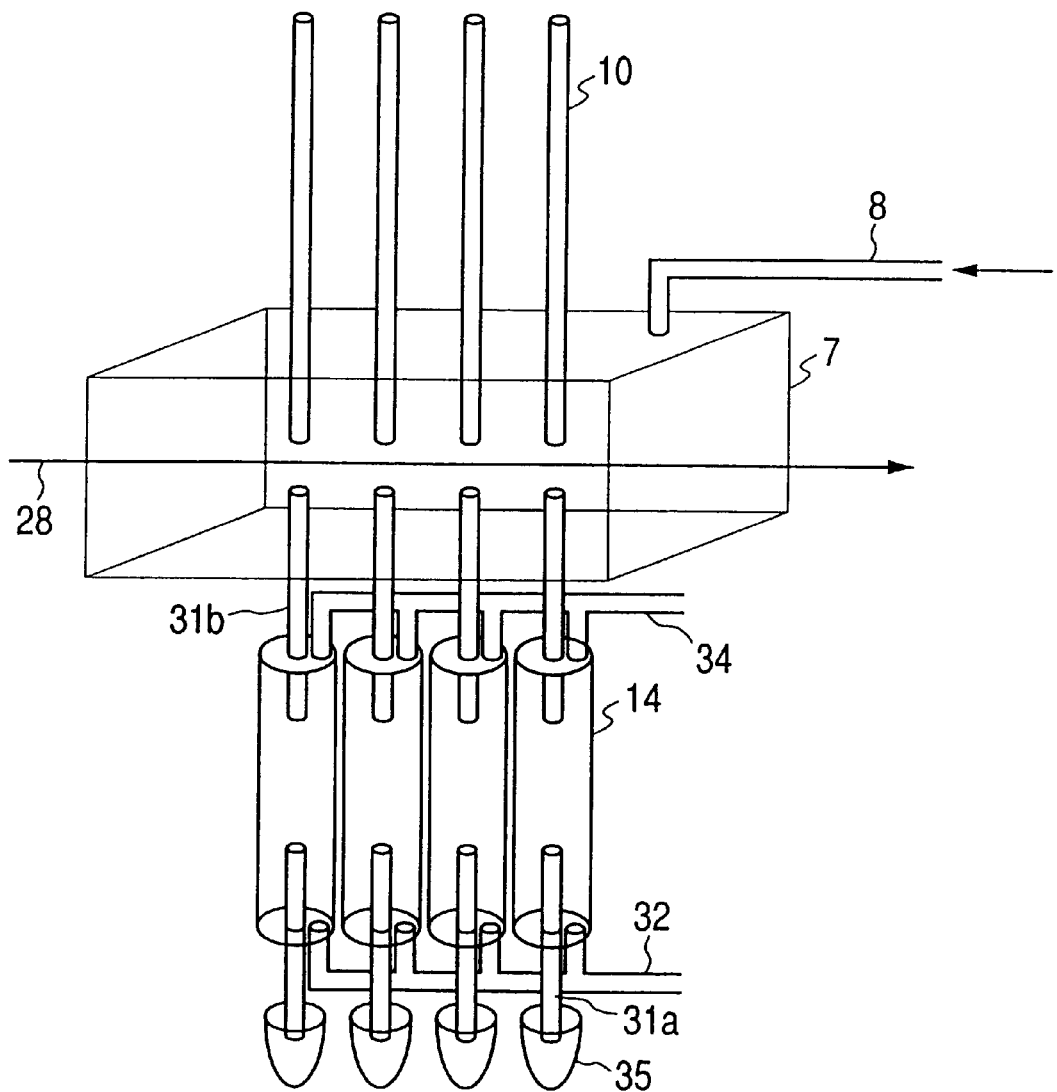
FIG. 7 is a diagram showing the optical cell and a third illustrative configuration of transferring means of the apparatus according to the first embodiment of the present invention.

FIG. 7 is a perspective view showing the optical cell and a third illustrative configuration of transferring means of the apparatus. In the configuration shown in FIG. 7, the sampling tubes 14 each have an inner diameter greater than the outer diameter of the capillaries, as in the configuration shown in FIG. 6, whereas additional tube 31*b* of the sampling tube 14 is arranged inside the optical cell 7 to sample the DNA fragments. This additional tube 31*b*has as short length as about 10 mm, and has identical inner and outer diameters with those of the capillary. According to this configuration, DNA fragments are sampled in the following manner: A buffer solution is introduced via tube 34 for introducing a buffer solution flowing through the sampling tube to form a sheath flow in the inside region of the sampling tube 14, the DNA fragments sampled in the vicinity of the center of the sampling tube are carried on the sheath flow via the additional tube 31*a* of the sampling tube to the sampling vessels 35 placed on the fraction collector. The buffer solution is drained via the drain tube 32. The structure of the transferring means becomes somewhat complicated because the sampling tube 14 is provided with the tube 34 for introducing the buffer solution and the drain tube 32, but the structure of the optical cell 7 can be simplified as compared with the configuration shown in FIG. 6.

Figure 8:
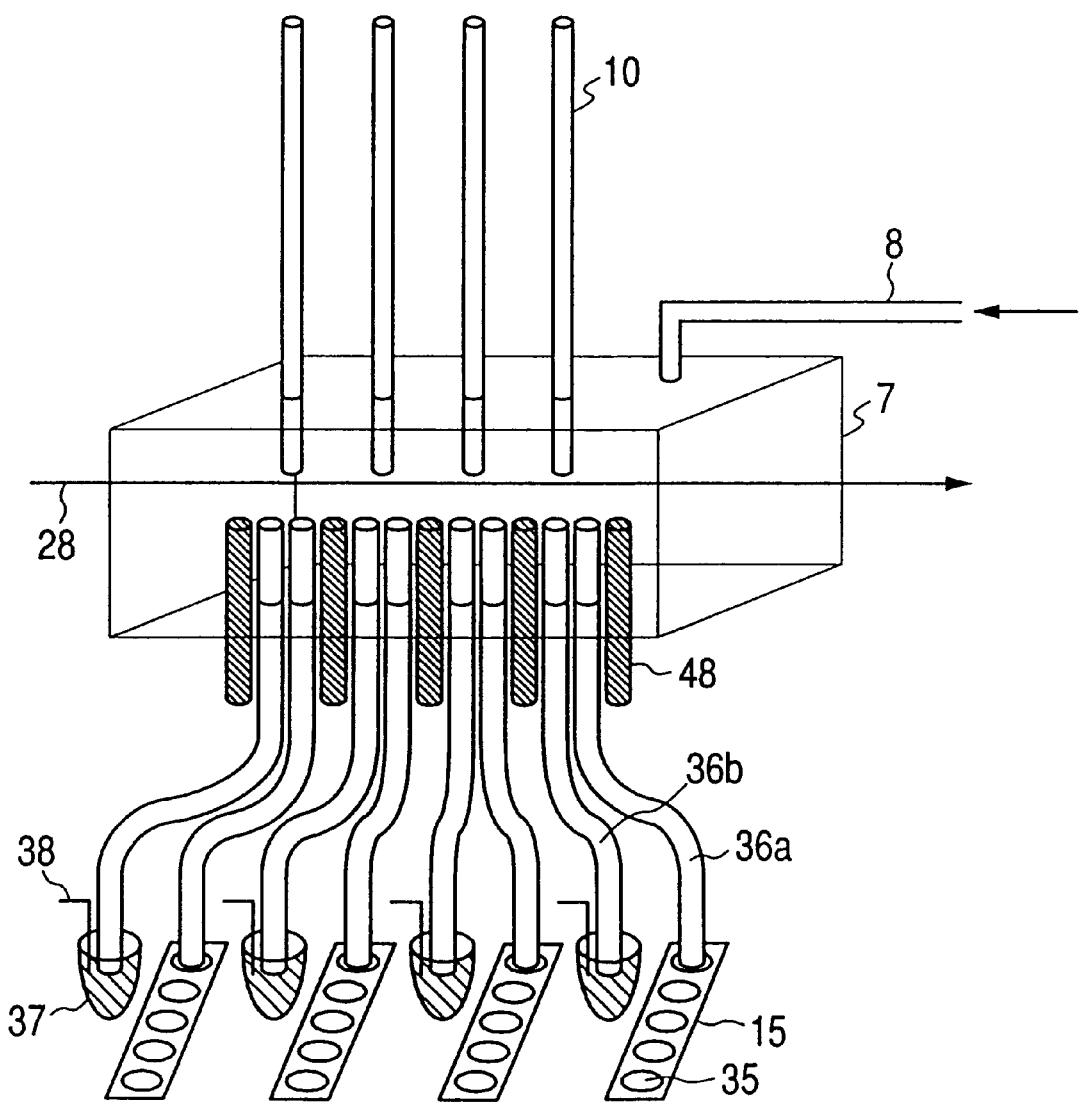
FIG. 8 is a diagram showing the optical cell a fourth illustrative configuration of and transferring means of the apparatus according to the first embodiment of the present invention.

FIG. 8 is a perspective view showing the optical cell and a fourth illustrative configuration of transferring means of the apparatus. In the configuration shown in FIG. 8, a pair of sampling tube 36*a* and drain tube 36*b*, which is interposed between glass rods 48, are arranged opposed to each capillary 10 at a certain gap in the inside region of the optical cell 7. All the glass rods 48, sampling tubes 36*a*, drain tubes 36*b* and capillaries 10 have an identical outer diameter with each other. According to the configuration shown in FIG. 8, DNA fragments are separated and sampled by using an electroosmic flow and switching sampling tubes, through which the DNA fragments flow, in the optical cell. The use of electroosmic flows can provide a laminar flow without friction, because an electric dual layer is formed on the boundary face between the buffer solution and the wall surface of the sampling tube due to electric charge of the wall surface. When the internal glass surfaces of the sampling tube 36*a* and the drain tube 36*b* have been subjected to a surface treatment to make electrically negative charged, the buffer solution is relatively positive charged in the inside regions of the sampling tube 36*a* and drain tube 36*b*, and an electroosmic flow from the optical cell toward outlet sides of the sampling tube 36*a* and drain tube 36*b* is formed by applying a negative voltage to the outlet sides of the sampling tube 36*a* and drain tube 36*b*. In this case, an earth is established for the optical cell 7 in common with respect to electrophoresis and transfer. To apply voltage to the outlet of the sampling tube, each of sampling vessels 35 placed on the fraction collector 15 holds a buffer solution in advance and has an electrode (not shown) arranged at its bottom.

When a target DNA fragment is detected, a voltage is applied to the electrode (not shown) arranged at the bottom of each sampling vessel 35 on the fraction collector 15 to apply a voltage to the outlet side of the sampling tube 36*a*, and hence the buffer solution in the inside region of the optical cell 7 flows into the sampling tube 36*a* more than the drain tube 36*b*. Consequently, the target DNA fragment can be introduced toward the sampling vessel 35 placed on the fraction collector 15. Next, other DNA fragments are introduced to the drain tube 36*b* by stopping applying the voltage to the sampling tube 36*b* and by applying a voltage to electrode 38 in drain 37 to apply a voltage to the drain tube 36*b*. The DNA fragments and buffer solution stored in the drain 37 are discarded. The DNA fragment once introduced into the sampling tube 36*b* can be sampled to the sampling vessels 35 placed on the fraction collector 15, since the buffer solution keeps flowing by gravity even after the voltage application to the sampling tube 36*a* is stopped.

Figure 9:
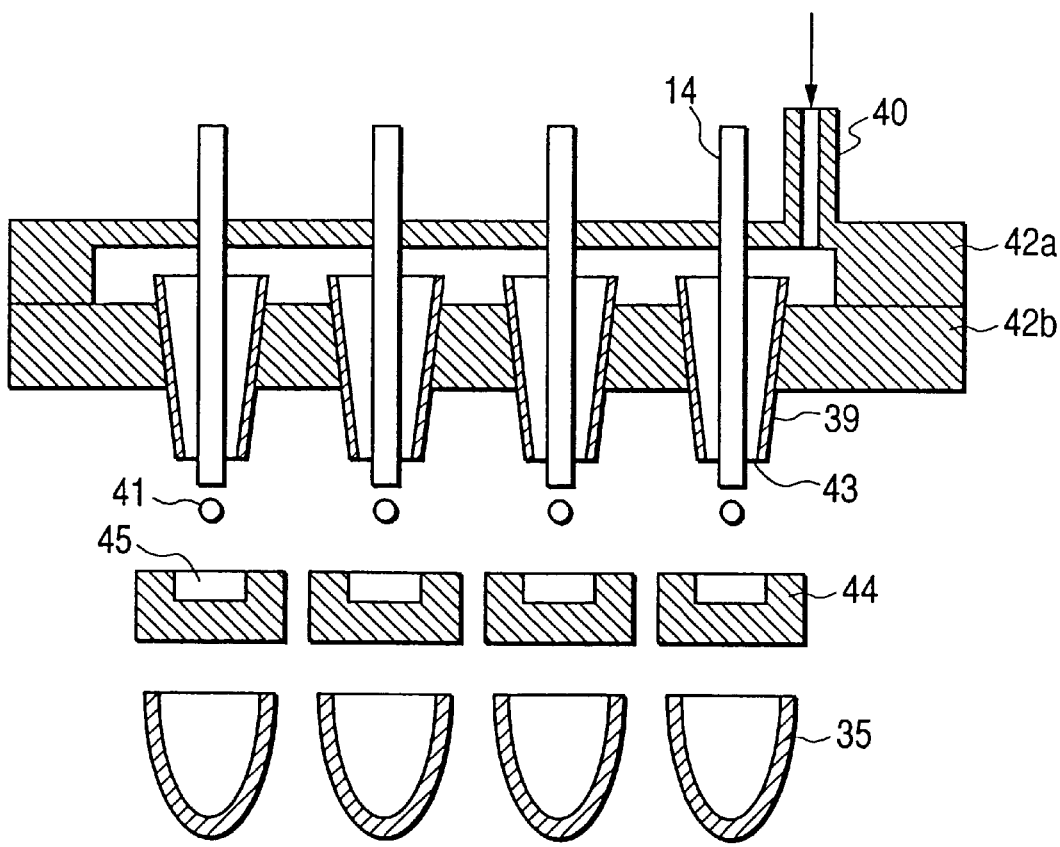
FIG. 9 is a diagram showing the optical cell a fifth illustrative configuration of and transferring means of the apparatus according to the embodiment of the present invention.

FIG. 9 is a diagram showing a fifth illustrative configuration of the transferring means of the apparatus. According to the configuration shown in FIG. 9, support 42*b* for conical shaped part is connected to support 42*a* for sampling tubes, which support 42*b* supports conical shaped part 39 having a hollow space to pass the end of the sampling tube 14, and which support 42*a* supports the outlet side of the sampling tube 14 illustrated in FIGS. 5A and 5B and has gas inlet 40. Through the gas inlet 40 is passed a gas ($N_2$, air) and issued in a jet from aperture 43 of the conical shaped part. The buffer solution containing DNA fragments transferred through the sampling tube 14 is formed to droplet 41 by the jet of gas issued from the aperture 43, carried by the gas flow and sampled to the sampling vessel 35 placed on the fraction collector. The sampling procedure is controlled by the movement of cover 44.

The end of the sampling tube 14 is arranged ejecting 2 mm to 3 mm from the aperture 43. The size (volume) of each droplet 41 can be set to about 0.1 $\mu$L, by adjusting the gas flow rate at the end of the conical shaped part 39 to about 10 m/sec. At a flow rate of the buffer solution flowing through the sampling tube of 10 mm/sec as described above and at an inner diameter of the capillary of 75 $\mu$m, the flow volume is about 45 nL/sec and one jet of the droplet is formed each 2 sec. Only when the target DNA fragment is detected, the cover 44 is removed to sample the droplets to the sampling vessel for a certain period of time. Otherwise, the droplets are stored in ditch 45 placed on the upper side of the cover 44 to discard to a drain (not shown). As a plurality of the sampling vessels 35 are provided on the fraction collector, corresponding to individual sampling tubes 14, a plurality of target DNA fragments can be sampled.

When the opening of each sampling vessel placed on the fraction collector 15 has a diameter of 6 mm, the distance from the end of the sampling tube to the opening of the sampling vessel should range within about 5 cm to ensure the sampling of sprayed droplets to the vessel. If the length of the sampling tube is set to 5 cm, the above mentioned distance can be as long as 10 cm. The fraction collector can therefore have a greater size and hence provide sampling with the use of a greater number of capillaries simultaneously than in the configurations where the DNA fragments are transferred directly through the sampling tubes 14. The spread in time of DNA fragments flowing through the sampling tube is about 5 sec in terms of half band width at a flow rate of the buffer solution flowing through the sampling tube of 10 mm/sec. Consequently, sampling two droplets nearly ensures sampling of a target DNA fragment alone.

Figure 10:
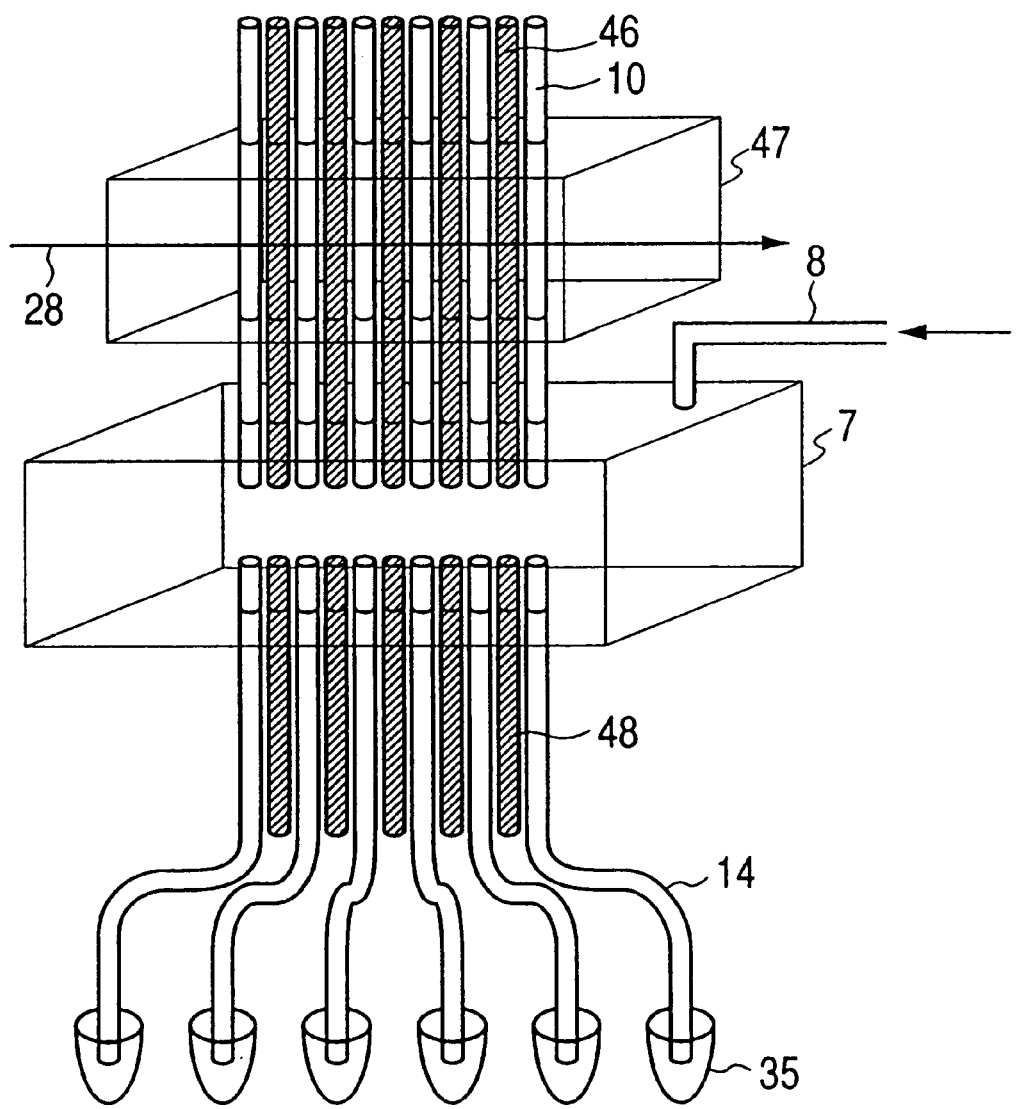
FIG. 10 is a perspective view showing an illustrative configuration of a detector of the DNA fragments of the apparatus according to the first embodiment of the present invention.

FIG. 10 is a perspective view showing an illustrative configuration of a detector of the DNA fragments of the apparatus. According to the configuration illustrated in FIG. 10, laser light 28 is applied directly and concurrently to a plurality of the capillaries 10 to detect a DNA fragment (on-column detection technique: for example, Japanese Patent Laid-open No. 9-288088). The detected DNA fragment further migrates to the end of the capillary 10 to elute into the inside region of the optical cell 7. The optical cell 7 may have a similar configuration to that illustrated in FIGS. 5A and 5B. After a lapse of time between the detection of the DNA fragment and initial elution of the DNA fragments from the end of the capillary, the target DNA fragment is collected. Alternately, scanning laser light may be applied to all the capillaries.

According to the configuration shown in FIG. 10, the capillaries 10 and rod lenses 46 are arranged in alternating sequence, and the resulting array of the capillaries 10 and the rod lenses 46 is fixed on quartz support 47 of the capillaries. The laser light 28 can penetrate the array to detect DNA fragments migrating through each of the capillaries 10. The DNA fragments eluted from each of the capillaries 10 are introduced into the sampling vessels 35 placed on the fraction collector through each sampling tube 14 arranged opposed to each capillary 10. Glass rods 48 are used for adjusting positions of the capillaries 10 relative to the sampling tubes 14. The glass rods 48 may have the identical shape and be composed of the identical materials to those of the rod lenses 46. According to the configuration shown in FIG. 10, the detection sensitivity for DNA fragments does not depend on the flow rate of the buffer solution flowing inside the optical cell, and the spread in time of the DNA fragments flowing through the sampling tube can be reduced by increasing the flow rate of the buffer solution. In addition, the flow rate of the buffer solution can also be increased by the use of a mechanical pump, since a slight instability of the flow due to the mechanical pump, if any, does not affect the detection performances of the DNA fragments.

Next, the configuration of the fraction collector will now be described in detail. A differentially expressed DNA which has been detected by the DD method or another expression profiling technique is identified by sequencing. The sampled DNA fragment is generally amplified by the PCR method in this procedure. The DNA fragments in the sample solution has, on average, a concentration of 10 fmol/$\mu$L to 0.1 fmol/$\mu$L. As the volume of the sample solution injected into the capillary is about 0.01 $\mu$L in actual measurement, the absolute amount of each DNA fragment ranges from $10^{-18}$ mol to $10^{-16}$ mol. This amount is sufficient at which amplification by the PCR method can sufficiently be conducted. Consequently, the sampling using capillary electrophoresis can satisfactorily be used in practice.

Figure 11:
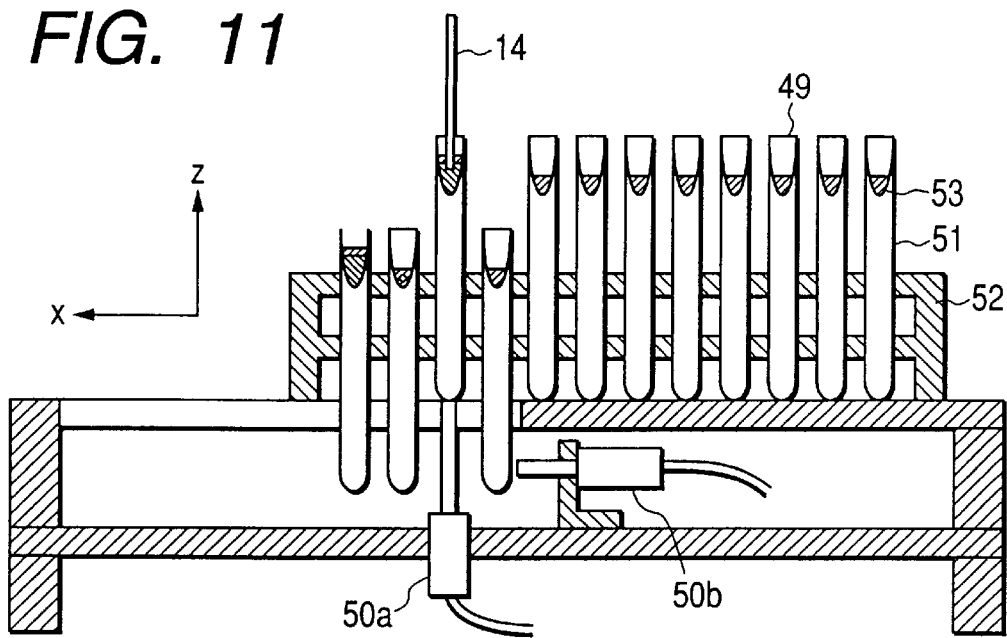
FIG. 11 is a cross sectional view showing a first illustrative configuration of a fraction collector of the apparatus according to the embodiments of the present invention.

FIG. 11 is a cross sectional view showing a first illustrative configuration of the fraction collector of the apparatus. The configuration shown in FIG. 11 uses sampling vessels 49 (0.2-mL PCR tubes) which are arranged at intervals of 9 mm. Such PCR tube are widely used as sampling vessels placed on a fraction collector. The PCR tubes are placed on holders 51 of sampling vessels. When DNA fragments are sampled from plural capillaries, the configuration shown in FIG. 11 only has to be arranged in a required number in the perpendicular direction to the plane of paper. A pair of two air-operation cylinders (51a, 51b) are used for each electrophoresis lane, the air-operation cylinder 51a is to actuate for vertical movement (in the direction of Z axis) and the air-operation cylinder 51b is to actuate for horizontal movement (in the direction of X axis). For actuation in the X axis direction, the configuration is arranged so that the individual holders 51 are connected with sliding stand 52, and once one holder 51 is pushed, the sliding stand 52 on the whole is moved in order to provide a great feed rate with respect to a short stroke of the cylinder. The stand is actuated in such a manner that the buffer solution containing the target DNA fragment is sampled into even-numbered tubes and unnecessary buffer solution is sampled into odd-numbered tubes. Mineral oil 53 has been charged in advance into each tube 49 to improve dropping off at the end of the sampling tube 14.

In combination use of a fraction collector having the configuration shown in FIG. 11 with the optical cell having the configuration shown in FIGS. 5A and 5B, about 1 $\mu$L buffer solution can be sampled in about 20 sec. When a buffer solution for PCR is charged in the even-numbered tubes in advance, the sampled DNA fragment is automatically placed into the tubes and PCR can be conducted by adding a polymerase or primer to the tubes and then immediately integrating the tubes into a PCR reactor.

The PCR tubes 49 can also be used as the sampling vessels 35 placed on the fraction collectors illustrated in FIG. 1, FIG. 4, FIGS. 6 through 10 and FIG. 12.

With an increasing number of the capillaries 10, demands have been made to miniaturize the fraction collector, and with a reducing volume of the fraction collector, the volumes of the sampling vessels 49 become insufficient to hold unnecessary buffer solution.

Figure 12:
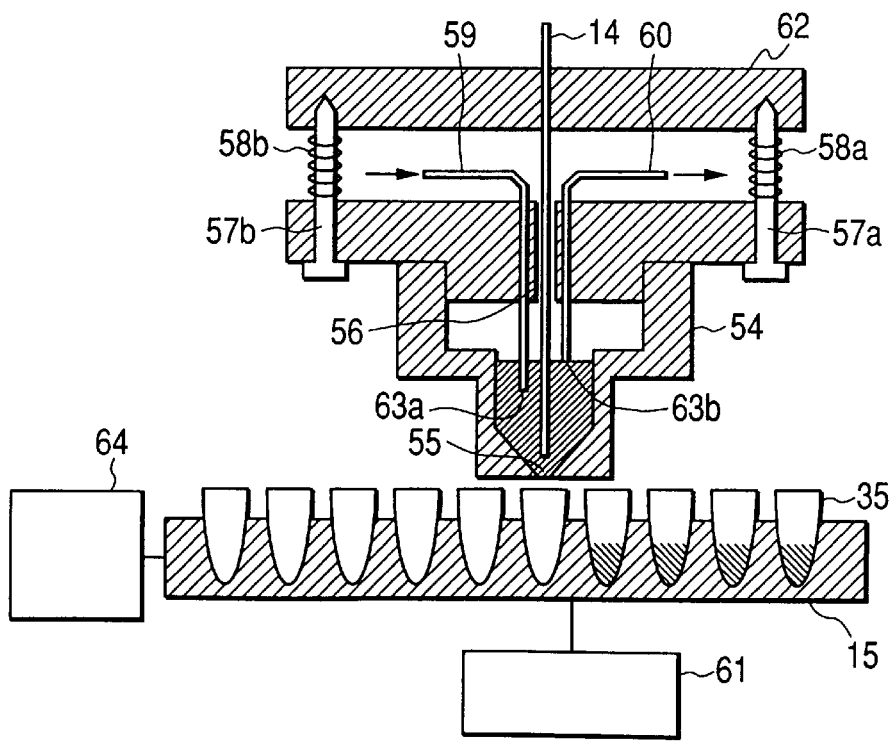
FIG. 12 is a cross sectional view showing a second illustrative configuration of a fraction collector of the apparatus according to the first embodiment of the present invention.

FIG. 12 is a cross sectional view showing a second illustrative configuration of the fraction collector of the apparatus. According to the configuration shown in FIG. 12, an excess or unnecessary buffer solution can be effectively treated. The sampling tube 14 as shown in FIGS. 5A and 5B is anchored into support 62 of sampling tubes, and is equipped with reservoir 54 at its end. The reservoir 54 has, at its bottom, aperture 55 having an inner diameter nearly equal to but slightly greater than the outer diameter of the sampling tube. The reservoir 54 has hole 56 having an inner diameter through which the sampling tube can be placed and moved smoothly, and is placed with the end of tube 59 for supplying purified water as a washing fluid to the reservoir 54 and the end of tubing 60 to the aspirator to exhaust the buffer solution and washing fluid in the reservoir 54.

When the DNA fragments are not sampled, the end of the sampling tube 14 is immersed in water (containing the solution buffer emitted from the sampling tube) reserved in the reservoir 54. When a target DNA fragment is sampled, the fraction collector 15 is lifted by actuator 61 for vertical movement and concurrently the reservoir 54 is lifted along guides 57a, 57b. As the sampling tube 14 is fixed to the support 62, its end is passed through the aperture 55 and inserted into the sampling vessel 35 placed on the fraction collector 15 when the reservoir 54 elevates. This state is retained for a given period of time to sample the buffer solution containing the target DNA fragment. After the sampling is completed, the fraction collector 15 descends, and subsequently the reservoir 54 descends along the guides 57a, 57b by means of the restoring force of springs 58a, 58b to return to the initial position. If another target DNA to be collected is detected, the sapling vessels 35 are shifted by one by the actuator 64 for horizontal movement, and the above procedure is repeated by the actuator 61 for vertical movement.

The washing fluid or purified water is supplied in order to maintain the ends of the sampling tubes 14 clean as far as possible and thereby to prevent contamination. The position of the outlet port 63b of the tubing 60 to the aspirator should be higher than that of inlet port 63a of the tube 59 for supplying purified water. The position of the outlet port 63b should be adjusted to a height that can prevent leakage of water in accordance with the size of the aperture 55. According to the configuration shown in FIG. 12, stable operation can be obtained without leakage from the aperture 55, when the height of the outlet port 63b is adjusted to 5 mm or less from the position of the aperture 55 at an outer diameter of the sampling tube of 200 $\mu$m and a diameter of the aperture 55 of 300 $\mu$m.

Figure 13:
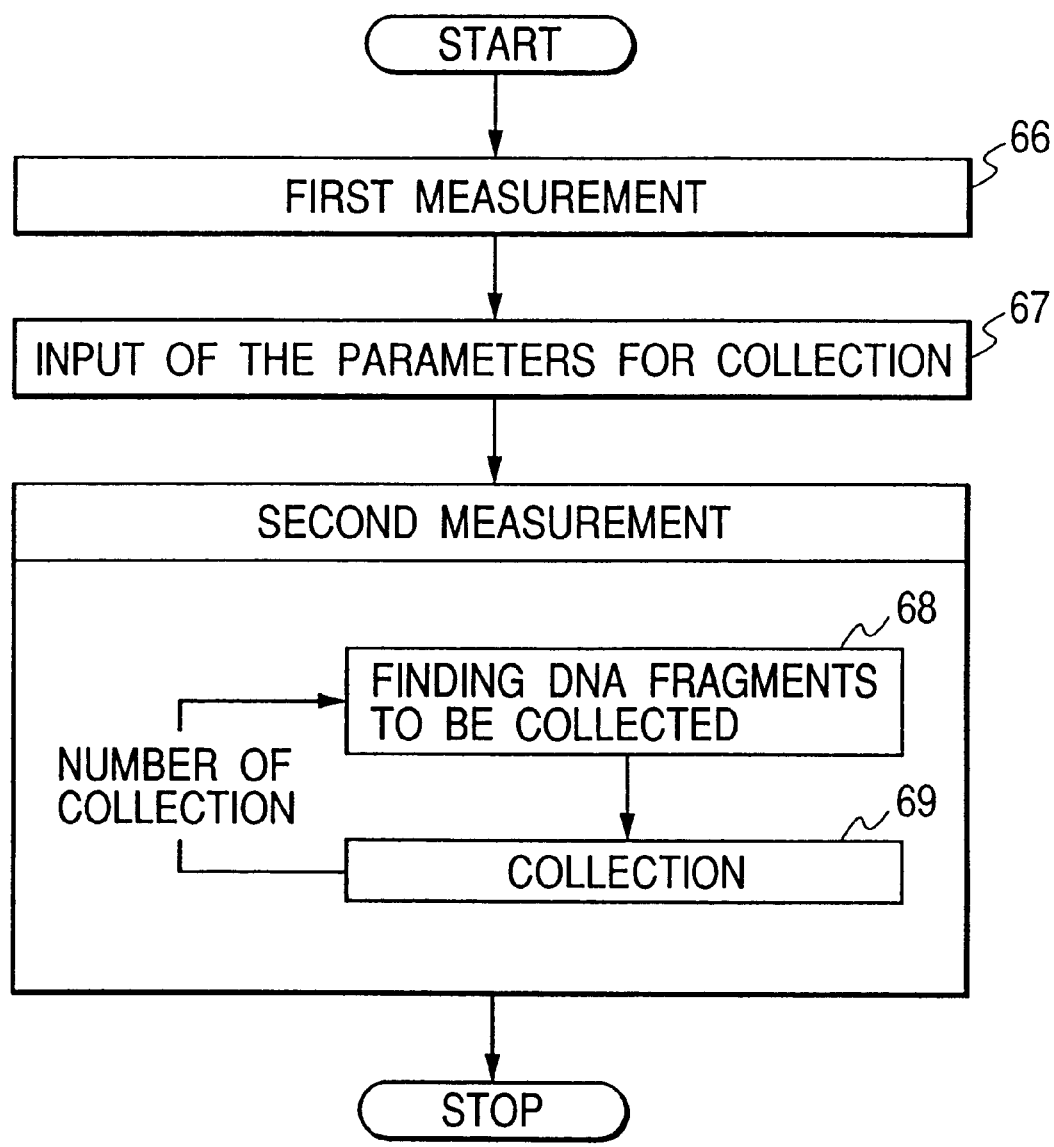
FIG. 13 is a flow chart showing steps for the separation and fractionation of DNA fragments using the apparatus according to the first embodiment of the present invention.

FIG. 13 is a flow chart showing steps for the separation and fractionation of the DNA fragments (differentially expressed gene) using the apparatus. Initially, a first electrophoresis is conducted to obtain an electropherogram (step 66). Based upon the obtained electropherogram, parameters for separation and sampling are determined (step 67). A plurality of samples are analyzed using a plurality of capillaries to give plural spectra (electropherograms) as shown in FIG. 3, and the electropherograms are compared among the samples to select differentially expressed DNA fragments. In this procedure, representation of a spectrum as shown in FIG. 3 is disadvantageous for the comparison among a multiplicity of samples.

Figure 14:
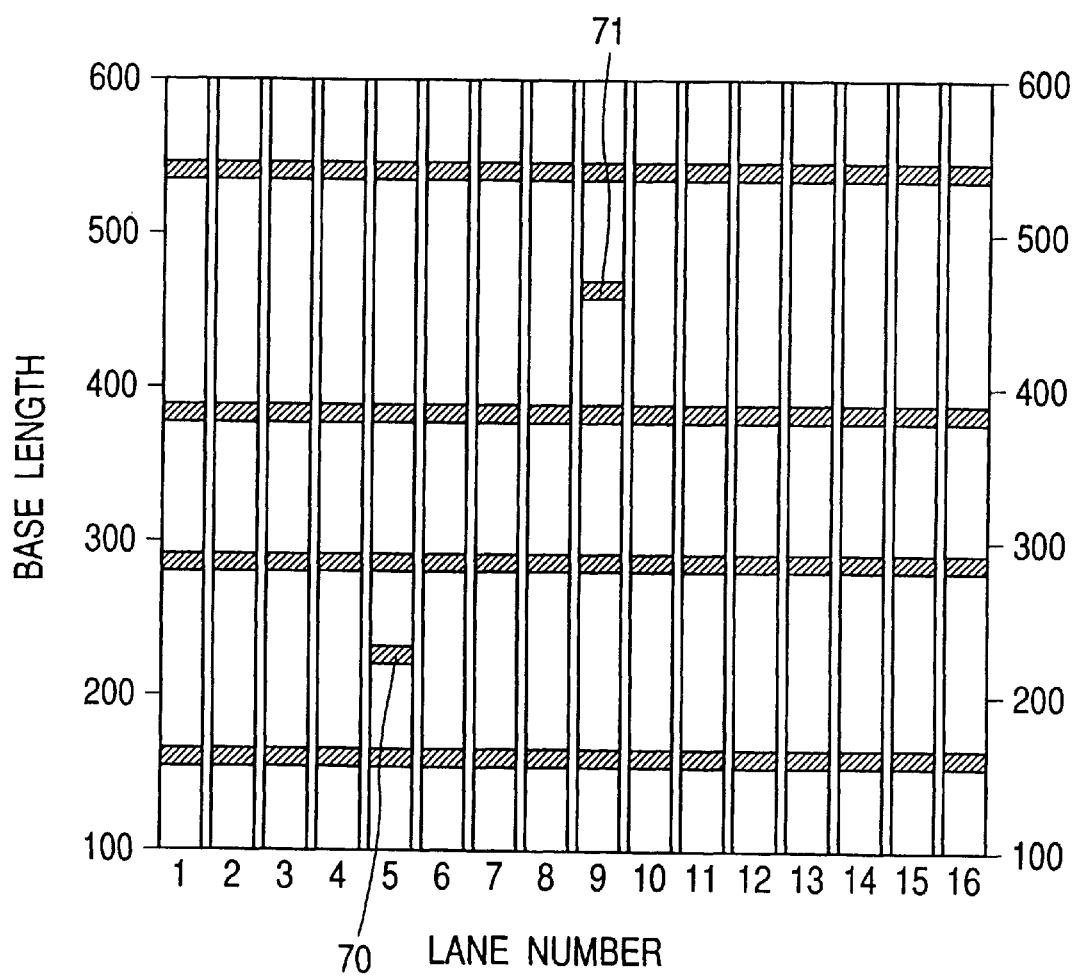
FIG. 14 is a diagram showing an illustrative display on a screen which is advantageous for detecting differentially expressed gene fragments using the apparatus according to the first embodiment of the present invention.

FIG. 14 is a diagram showing an illustrative display on a screen, which is advantageous for detecting differentially expressed gene fragments using the inventive apparatus. As schematically illustrated in FIG. 14, the intensities of the DNA bands of individual lanes are indicated by bars of 256-step gray scale, aligned and displayed on the screen of an output device to facilitate the comparison. The illustrated indication in FIG. 14 is similar to an image obtained by reading out the image of a slab gel with an image reader, whereas the use of this indication can provide a comparison in base length with a higher precision, because the results as indicated are calibrated for each capillary by a marker DNA. In the illustrative indication shown in FIG. 14, specific bands (differentially expressed genes) 70, 71, which are not observed in the other lanes, are respectively observed in the lane No. 5 and lane No. 9. When the bands 70, 71 are designated on the display, parameters for collection are input automatically.

After inputting the parameters for collection, a second electrophoresis is conducted to find DNA fragments to be collected in the measurement (step 68), and the fraction collector is actuated to collect the target DNA fragments (step 69), as illustrated in FIG. 13. The steps 68 and 69 are repeated per each capillary a set number of times, which is the same with the number of peaks to be collected.

The first and second electrophoresis should preferably be carried out in the identical electrophoreses parameters, whereas the parameters can be changed within the range as far as not markedly affecting the peak patterns after converted to base lengths. In particular, by increasing the migration rate of the first electrophoresis to shorten the measurement time, and decreasing the migration rate of the second electrophoresis to increase the separation time on a gel, the precision in separation is increased and the time for measurement is shortened on the whole. In the step 68, the DNA peaks selected in the step 67 are found while electrophoresing. To find the target DNA peaks, migration times of the target peaks or differences between the migration times and those of the marker peaks obtained in the first measurement can be used. The DNA peaks can be also found from peak patterns by, for example, using the number of peaks or a coefficient of correlation between the measured data in the first measurement.

Figure 15:
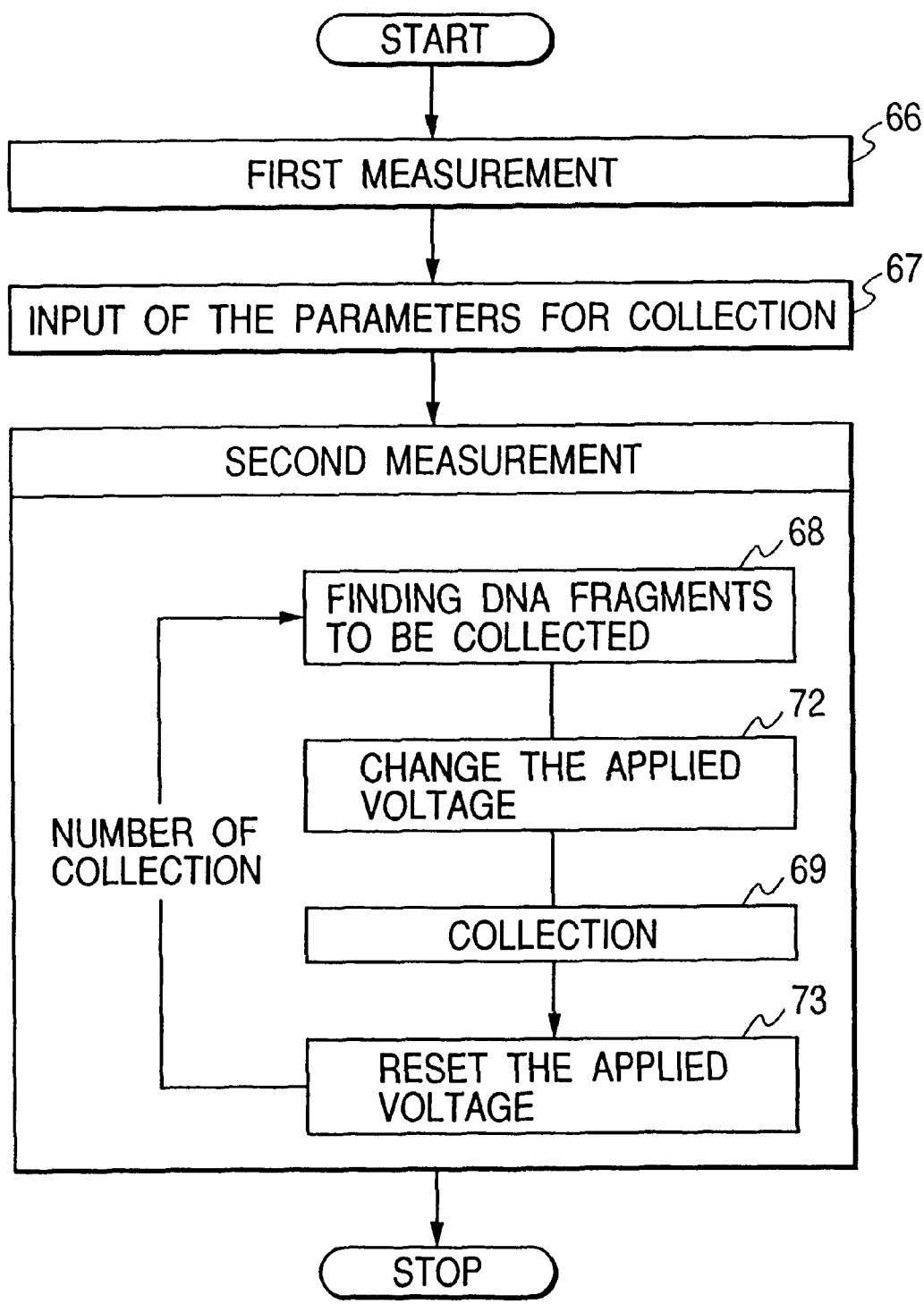
FIG. 15 is a flow chart showing a step for shortening the required time for the separation and fractionation of DNA fragments with the use of the apparatus according to the first embodiment of the present invention.

FIG. 15 is a flow chart showing steps for shortening the required time for the separation and fractionation of DNA fragments with the use of the inventive apparatus. According to the procedure shown in FIG. 15, step 72 to change the applied voltage and step 73 to reset the applied voltage after sampling are added to the second electrophoresis for collecting the DNA fragments in the steps for collection illustrated in FIG. 13. Through the steps 72 and 73, the migration rate is decreased (the migration voltage is decreased) on the sampling of the DNA fragments for improving the precision in separation, and the migration rate is increased (the migration voltage is increased) upon other steps than the sampling. The required time for the separation by electrophoresis can therefore be shortened.

At other times than the sampling of the DNA fragments, defining a migration voltage as v, a time interval for the measurement of fluorescence (sampling interval) as $t_s$, a gathering time of fluorescence as $t_g$ and obtaining an electropherogram with the abscissa being a migration time= sampling times$\times t_s$ and the ordinate being a fluorescent intensity I obtained during the gathering time $t_g$ of fluorescence, target DNA fragments are sampled by inputting, for example, a migration voltage v'=0.5 v, a time interval for measuring fluorescence (sampling interval) $t_s'$= $2t_s$, and a gathering time for fluorescence $t_g'=2t_g$ in synchronism with the start of sampling of the target DNA fragments. The migration voltage, time interval for measuring fluorescence (sampling interval) and gathering time of fluorescence are reset to v, ts and tg, respectively, in synchronism with the completion of sampling of the target DNA fragments. When the target DNA fragments are sampled, an electropherogram with the abscissa being a migration time=sampling times$\times t_s$ and the ordinate being an fluorescent intensity I obtained in the gathering time of fluorescence $t_g$ can nearly be reproduced while defining a migration voltage as v, a time interval for the measurement of fluorescence (sampling interval) as $t_s$, a gathering time of fluorescence as $t_g$, by determining electropherograms with abscissa a migration time=sampling times$\times t_s'$ and the ordinate a fluorescent intensity I obtained during the gathering time $t_g'$ of fluorescence. The above mentioned procedure can prevent adverse effects on the calibration or conversion from migration times to base lengths by the marker, and adverse effects on the finding of peaks to be collected in sampling of a plurality of DNA fragments in the identical migration lane or different migration lanes. In this connection, the technique of improving the detection sensitivity by periodically changing the migration voltage and exposure time (gathering time for fluorescence) is a known technique (Japanese Patent Laid-open No. 9-127058).

Figure 16:
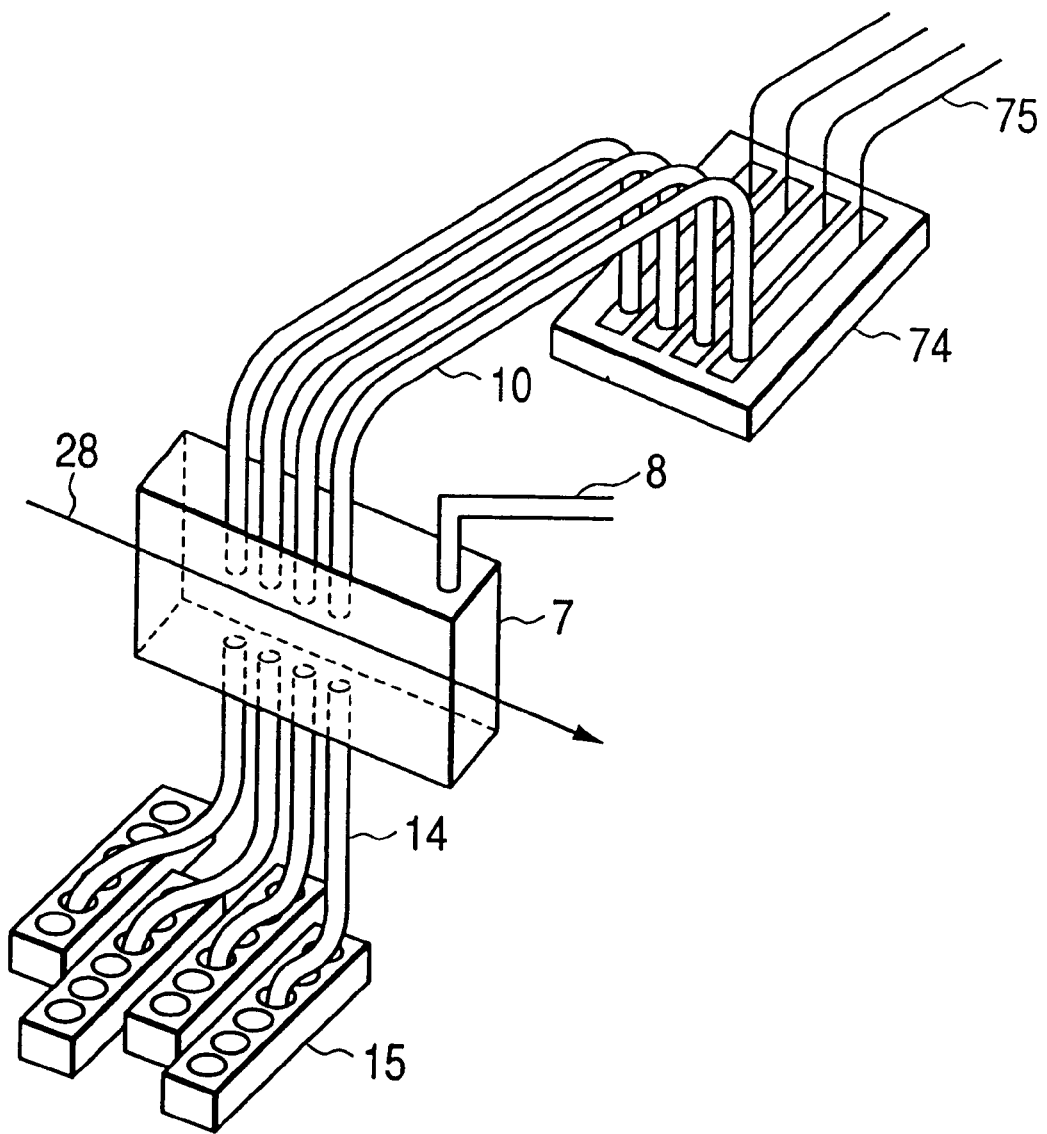
FIG. 16 is a diagram illustrating the configuration of an apparatus for the separation and fractionation according to a third embodiment of the present invention, which can shorten the required time for the separation and fractionation of DNA fragments.
Figure 17A:
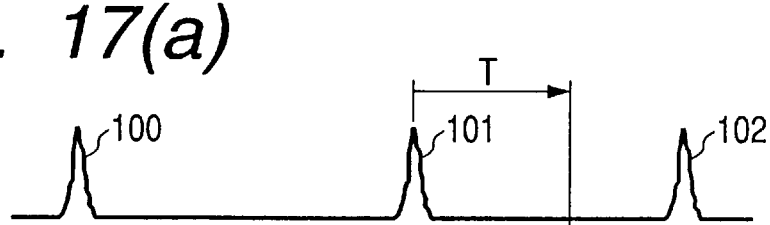
FIG. 17 is a diagram showing a process, using a marker, of finding a DNA fragment to be collected by the apparatus according to the embodiment of the present invention.
Figure 17B:
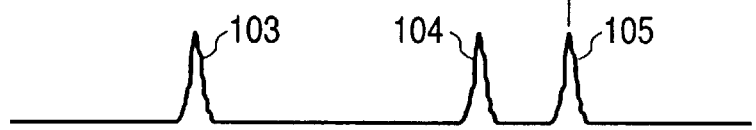
Figure 17C:
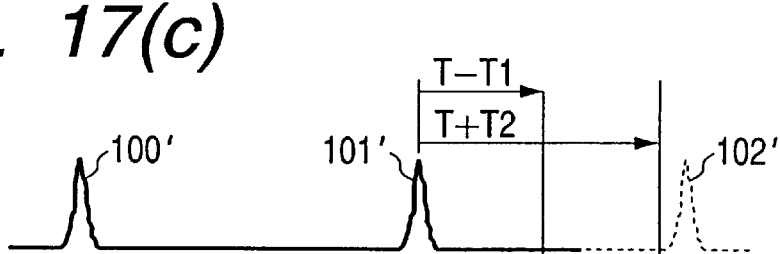
Figure 17D:
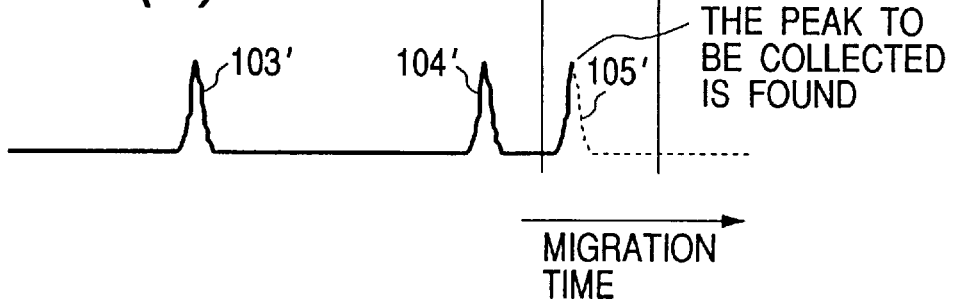

FIG. 16 is a diagram illustrating the apparatus for the separation and fractionation according to the third embodiment of the invention, which configuration can shorten the required time for the separation and fractionation of DNA fragments. In the configuration shown in FIG. 16, buffer reservoir 74 for electrophoresis is composed of a plurality of split grooves, and individual ends of the capillaries 10 and individual electrodes 75 are placed in the individual grooves independently. In the steps 72 and 73 demonstrated in FIG. 15, individual migration voltages are independently changed upon the detection of the target DNA fragments in the individual capillaries.

According to a modified embodiment, DNA fragments can be automatically separated and sampled by electrophoresing a plurality of samples through one capillary, which samples are independently labeled with different fluorophores and by detecting DNA fragments present in a sample from the difference in fluorescent intensities. The measuring time on the whole can be shortened since measurement and collection are carried out simultaneously in one measurement. After sampling the DNA fragments, data are analyzed again, and fractions containing DNA fragments which are found to have significant differences are sampled and subjected to amplification by PCR, followed by sequencing.

According to another modified embodiment, the volume of the sample consumed by electrophoresis on capillary is several ten nanoliters and thus can be neglected as compared with the volume of the sample solution used in the injection of the sample (several microliters), and another analysis can be carried out by using the remained sample again. In this procedure, the marker DNA is not mixed with the sample DNA and they are independently injected to the capillaries in the same manner as in FIG. 2 in order to prevent the sample from contamination.

The inventive apparatus is provided with the marker tray 12' and the sample tray 12 as illustrated in FIG. 1. The marker tray 12' is to support the wells 16' for holding marker solutions 18' which is to be injected into all the capillaries in common, and the sample tray 12 is to support the wells 16 for holding different sample solutions per individual capillaries. The procedure of injecting the sample as described above with reference to FIG. 2 is repeated twice while switching the electrodes 20, 20' and thereby the marker solutions and the sample solutions are respectively injected into each capillary and then electrophoresed to give an electropherogram as is illustrated in FIG. 3. Where necessary, time lag between the injection of the marker and the injection of the sample is calibrated upon the analysis of electropherograms.

According to yet another modified embodiment, differentially expressed DNA fragments are detected by the use of the results of the above-mentioned electropherograms alone and the samples alone containing the differentially expressed DNA fragments are selected, and the selected DNA fragments can be separated and sampled by electrophoresis on a slab gel and cutting out of bands in the same manner as in conventional technologies. The procedure according to this embodiment cannot be completely automatized, but it is practically useful as a screening means for the separation and fractionation of samples using conventional technologies, since the number of samples from which differentially expressed DNA fragments are obtained may often be comparatively smaller than that of all the samples prepared in the DD method, for example.

According to the present invention, target DNA fragments can be separated from other DNA fragments and sampled by electrophoresing and, by the control means, separating a marker with the DNA fragments and finding DNA fragments to be collected based upon the time when the marker is detected and controlling the sampling means based upon signals gained when the target DNA fragments are detected. The procedure will be now described in detail below.

FIG. 17 is a diagram showing a process, using a marker, of finding DNA fragments to be collected by means of the apparatus according to the embodiment of the present invention. Initially, an electropherogram (electropherogram (a) in FIG. 17) of the marker and an electropherogram (electropherogram (b) in FIG. 17) of the sample are obtained simultaneously by the first measurement, by injecting a mixture of the marker and sample or injecting the marker and sample separately in two installments into the capillary. Next, the sample and marker are injected again for the second measurement, and in this step, the peak to be collected is automatically found based upon the measured data in the first measurement and with reference to the peak of the marker. Electropherograms (c) and (d) in FIG. 17 respectively show electropherograms of the marker and of the sample obtained by the second measurement. In the electropherogram (a) in FIG. 17, peaks 100, 101, 102 are marker peaks and peaks 103, 104, 105 are samples peaks. Peaks 100', 101', 102', 103', 104', 105' in the electropherograms (c) and (d) are peaks obtained by the second measurement and respectively correspond to the peaks obtained by the first measurement. The peak 101 is a peak to be a time base for the peak 105 designated to be collected, the peak 101' is a peak to be a time base when the peak to be collected is found, and the peak 105' is the peak to be collected.

After the first measurement, when the peak 105 is designated to be collected, the peak is found within the time range between (T−T1) and (T+T2) on the basis of the timing when the marker peak 101 is detected in the second measurement, and a signal to start the controller 9 (FIG. 1) is produced. The timing when the peak to be collected is found may be set at the maximum point of the peak or at a timing when the peak crosses a given threshold. Time T is time lag between the peaks 101 and 106 obtained by the first measurement, and T1 and T2 are predetermined values. The values T1 and T2 should preferably be minimized in order to prevent contamination of other peaks than the target peak 105 to be collected, whereas they may range from about 0.5% to 5% of T, in accordance with the reproducibility between the first measurement and the second measurement or with separation of adjacent peaks.

The first and second measurements should preferably be conducted with identical parameters for migration (lengths of gel capillaries, separation medium, migration voltage) with each other, whereas data of electropherograms of the marker obtained at varying parameters in advance can also be utilized. To be more specific, The time lag T between the marker peak 101 and the peak 105 designated to be collected is obtained by the first measurement, and is converted to T' which corresponds to the parameters for migration in the second measurement, and the peak is found in the time range from (T−T1) to (T+T2). This process is particularly effective when a target DNA fragment is separated and sampled by screening a multiplicity of samples in the first measurement to select a sample alone which contains the peak to be collected, and subjecting the selected sample to the second measurement. In the first measurement, peak patterns are obtained at high migration rate with high migration voltage and/or short capillaries, and in the second measurement the target DNA fragment is collected at low migration rate with low migration voltage and/or long capillaries, resulting in high separation. The working efficiency on the whole can therefore be improved without deteriorating the separation in collection.

In the process shown in FIG. 17, the marker peak 101 migrating immediately before the peak 105 to be collected is used as a base peak for finding the peak 105, whereas another peak having a shorter migration time than the peak 105, for example the peak 100, can also be used as the base peak.

However, the use of a marker peak migrating immediately before the peak to be collected is preferable, as far as giving no problem such as noises in the measurements or speed of analysis, to prevent errors in finding the peak 105 designated to be collected.

In the pattern (c) of FIG. 17, the marker peak can accurately be found with reducing the effects of noises or other errors in the measurements, by using data on relationship between peak patterns of the marker which have been obtained at varying parameters in advance and their migration times, and assessing whether the given marker peak is detected within the given range of migration time. Furthermore, according to the AFLP method, end bases are selected upon PCR, and the base lengths of some peaks to be collected may be estimated in advance. This method is advantageous because the time lag T of the target DNA fragment with respect to the marker peak can easily be estimated from the data of peak patters of the marker, without conducting the first measurement.

The process for controlling the sampling means with the use of a marker is described above, whereas the sampling means can also be controlled without the use of a marker and target DNA fragments can be separated and sampled from other DNA fragments. This process will be described in detail below.

Figure 18A:
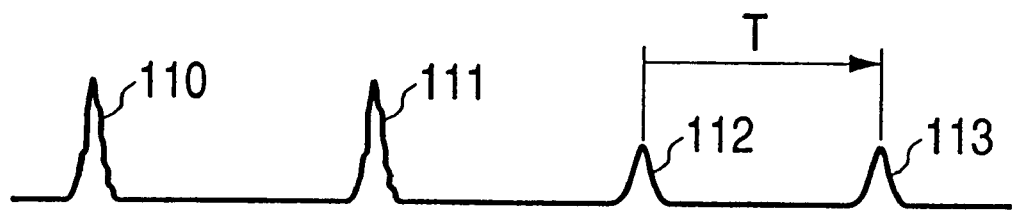
FIG. 18 is a diagram showing a process, without using a marker, of finding a DNA fragment to be collected by the apparatus according to the embodiment of the present invention.
Figure 18B:
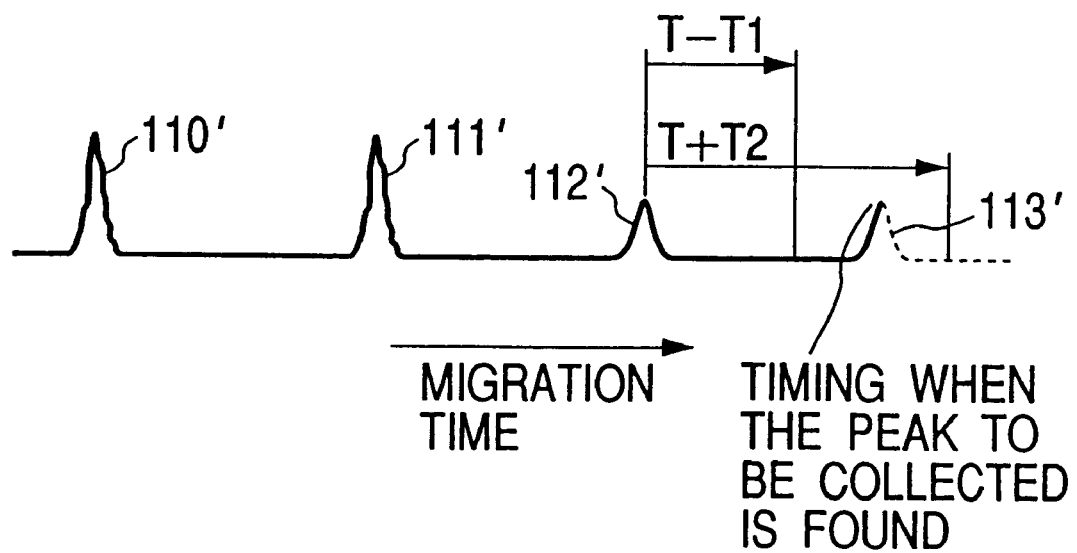

FIG. 18 is a diagram showing a process for finding a target DNA fragment to be collected without using a marker by the apparatus according to the embodiment of the invention, in which a peak to be collected is found based upon the peak pattern of the sample itself.

Patterns (a), (b) in FIG. 18 respectively illustrate electropherograms in the first and second measurements. In the first measurement, peak 113 to be collected is designated, and concurrently one or plural base peaks (peaks 110, 111 and 112 in the electropherogram (a) of FIG. 18) which are migrated ahead of the peak to be collected are selected. In this figure, the peak 113 is a peak designated to be collected, the peak 112 is a peak to be a time base for finding the peak to be collected, the peak 113' is the peak to be collected, and the peak 112' is a peak to be a time base for finding the peak to be collected. The selected base peaks are treated in the same manner as the marker peak shown in the pattern (c) of FIG. 17. To be more specific, using time lag T in migration between the peak 113 to be collected and the base peak 112 migrating immediately before the peak 113, the peak 113' to be collected is found in the elapsed time range from (T−T1) to (T+T2) after the base peak 112' is detected in the second measurement (the pattern (b) of FIG. 18). In this step, the base peaks 110', 111' are found by finding peaks detected within a given range of migration times in the second measurement, which time range is determined based upon the migration times of peaks 110, 111 obtained by the first measurement, in order to find exactly the base peak 112' without confusing with another peak. Both the process of using a marker as a base (FIG. 17) and the process of using a sample itself as a base (FIG. 18) can concurrently be employed in combination. Thus, the peak to be collected can be found with more reliability by selecting a base peak which has high intensity and is satisfactorily separated from another adjacent peak in accordance with peak patterns.

Other embodiments and variations will be obvious to those skilled in the art, and this invention is not to be limited to the specific matters stated above.

What is claimed is:

1. An apparatus for the separation and fractionation of differentially expressed gene fragments, the apparatus comprising:
   a separating means including a capillary filled with a separation medium to separate DNA fragments by electrophoresis, the DNA fragments each being labeled with a fluorophore;
   a detecting means to apply laser light to the DNA fragments separated in the capillary and to detect fluorescence emitted from the fluorophore;
   a means to form a sheath flow of a buffer solution to carry the separated DNA fragments eluted from the end of the capillary;
   a sampling means including sampling vessels to fractionate and sample the separated DNA fragments, according to their size;
   a transferring means to transfer the buffer solution containing the separated DNA fragments to the sampling means, the transferring means including
      a sampling tube which is disposed such that its end opposes the end of the capillary at a specified gap,
      a means to form droplets of buffer solution containing the separated DNA fragments, and
      a transporting means to transport the formed droplets to the sampling vessels by gas flow; and
   a control means to control the sampling means based on a signal gained by the detecting means;
   wherein the separated DNA fragments are transferred to the opening of the end of the sampling tube; and
   wherein a voltage for the electrophoresis and a length of the capillary are adjusted such that a spread in time of the separated DNA fragments caused by the transferring means during the transfer of the separated DNA fragments to the sampling vessels is smaller than a difference in separation time of the DNA fragments in the separating means.

2. An apparatus according to claim 1, wherein the laser light is applied to the gap.

3. An apparatus according to claim 1, wherein the laser light is applied to the capillary.

4. An apparatus according to claim 1, wherein the separating means includes a plurality of the capillaries; and
   wherein the apparatus further comprises a voltage applying means to apply a voltage for electrophoresis to each of the capillaries independently.

5. An apparatus according to claim 1, wherein the separating means includes a plurality of the capillaries;
   wherein the apparatus further comprises a voltage applying means to apply a voltage for electrophoresis to each of the capillaries independently;
   wherein the voltage applying means sets the voltage for electrophoresis during a period when the separated DNA fragments are sampled to be smaller than the voltage for electrophoresis during a period wherein the separated DNA fragments are not sampled; and
   wherein the detecting means sets, in synchronism with the start of a period for sampling the separated DNA fragments, a sampling interval of the fluorescence and a time for for gathering the fluorescence to be respectively greater than a sampling interval of the fluorescence and a time for gathering the fluorescence during a period when the separated DNA fragments are not sampled.

6. An apparatus for the separation and fractionation of differentially expressed gene fragments, the apparatus comprising:
   a separating means including a capillary filled with a separation medium to separate DNA fragments by electrophoresis, the DNA fragments each being labeled with a fluorophore;
   a detecting means to apply laser light to the DNA fragments separated in the capillary and to detect fluorescence emitted from the fluorophore;
   a means to form a sheath flow of a buffer solution to carry the separated DNA fragments eluted from the end of the capillary;
   a sampling means including sampling vessels to fractionate and sample the separated DNA fragments, according to their size;
   a transferring means to transfer the buffer solution containing the separated DNA fragments to the sampling means, the transferring means including a sampling tube which is disposed such that its first end opposes the end of the capillary at a specified gap, the separated DNA fragments being transferred to the opening of the first end of the sampling tube;
   a reservoir, having disposed therein a second end of the sampling tube, to contain the buffer solution eluted from the second end of the sampling tube, the reservoir having, at its bottom, an aperture having such a diameter that the sampling tube can be placed therethrough;

a first tube to transport a washing fluid to the reservoir;

a second tube to drain the buffer solution from the reservoir; and a control means to control the sampling means based on a signal gained by the detecting means;

wherein the second end of the sampling tube is placed through the aperture to transport the separated DNA fragments transferred by the sampling tube to the sampling vessels; and wherein a voltage for the electrophoresis and a length of the capillary are adjusted such that a spread in time of the separated DNA fragments caused by the transferring means during the transfer of the separated DNA fragments to the sampling vessels is smaller than a difference in separation time of the DNA fragments in the separating means.

7. An apparatus for the separation and fractionation of differentially expressed gene fragments, the apparatus comprising:

a separating means including a plurality of capillaries each filled with a separation medium to separate DNA fragments by electrophoresis, the DNA fragments each being labeled with a fluorophore;

a voltage applying means to apply a voltage for electrophoresis to each of the capillaries independently;

a detecting means to apply laser light to the DNA fragments separated by each of the capillaries and to detect fluorescence emitted from the fluorophore;

a means to form a sheath flow of a buffer solution to carry the separated DNA fragments eluted from the end of each of the capillaries;

a sampling means including sampling vessels to fractionate and sample the separated DNA fragments, according to their size;

a transferring means to transfer the buffer solution containing the sampled DNA fragments to the sampling means, the transferring means including a sampling tube which is disposed such that its end opposes the end of each of the capillaries at a specified gap, the separated DNA fragments being transferred to the opening of the end of the sampling tube; and a control means to control the sampling means based on a signal gained by the detecting means;

wherein the voltage applying means changes the voltage during electrophoresis based on the signal gained by the detecting means; and wherein the voltage for the electrophoresis and a length of each of the capillaries are adjusted such that a spread in time of the separated DNA fragments caused by the transferring means during the transfer of the separated DNA fragments to the sampling vessels is smaller than a difference in separation time of the DNA fragments in the separating means.

8. An apparatus for the separation and fractionation of differentially expressed gene fragments, said apparatus comprising:

a separating means including a capillary filled with a separation medium to separate DNA fragments by electrophoresis, said DNA fragments each being labeled with a fluorophore, a detecting means to apply laser light to the DNA fragments separated by the capillary and to detect fluorescence emitted from the fluorophore, a transferring means including a sampling tube which is placed with its first end opposed to the terminal end of the electrophoresis capillary at a specified gap, said separated DNA fragments being transferred to the opening of said first end, a means to form a sheath flow of a buffer solution to carry the separated DNA fragments eluted from the capillary to the opening of said first end, a sampling means having sampling vessels to fractionate and sample said DNA fragments according to their sizes, said DNA fragments transferred by the sampling tube, and a control means to control the sampling means based on a signal gained by the detecting means, wherein said sampling tube has an inner diameter greater than the outer diameter of said capillary.

9. An apparatus for the separation and fractionation of differentially expressed gene fragments, comprising:

a separating means including a capillary filled with a separation medium to separate DNA fragments by electrophoresis, said DNA fragments each labeled with a fluorophore, a detecting means to apply laser light to the separated DNA fragments by the capillaries and to detect fluorescence emitted from the fluorophore, a first tray to hold wells for holding a sampling solution containing said DNA fragments, a second tray to hold wells for holding a marker solution each containing a marker, an injecting means to inject said sample solution and said marker solution into said capillary separately, a transferring means including a sampling tube which is placed with its first end opposed to the end of the electrophoresis capillary at a specified gap, said separated DNA fragments being transferred to the opening of said first end, a means to form a sheath flow of a buffer solution to carry the separated DNA fragments eluted from said capillary to the opening of the first end, a sampling means including sampling vessels to fractionate and sample the DNA fragments transferred by the sampling tube according to their sizes, and a control means to control said sampling means based on a signal gained by said detecting means, wherein the sampling tube has a length ranging from 5 cm to 15 cm and an inner diameter ranging from 50 $\mu$m to 100 $\mu$m, and wherein said buffer solution flowing through the sampling tube has a flow rate of about 10 mm/sec.

10. An apparatus according to claim 9, wherein the transferring means further includes:

a means to form droplets of the buffer solution containing the separated DNA fragments transferred by the sampling tube; and a transporting means to transport the formed droplets to the sampling vessels by gas flow.

11. An apparatus according to claim 9, further comprising a reservoir placed with a second end of said sampling tube to contain the buffer solution eluted from the second end, said reservoir having an aperture at its bottom, said aperture having such a diameter that said sampling tube can be placed therethrough, a first tube to transport a washing fluid to said reservoir, and a second tube to drain the buffer solution from said reservoir, wherein the second end of the sampling tube is placed through said aperture to transport the DNA fragments transferred by the sampling tube to said sampling vessels.

12. An apparatus according to claim 9, wherein said laser light is applied to said gap.

13. An apparatus according to claim 9, wherein said laser light is applied to said capillary.

14. An apparatus according to claim 9, wherein said separating means includes a plurality of said capillaries and wherein said apparatus further comprises a voltage applying means to apply a voltage for electrophoresis to each of said capillaries independently.

15. An apparatus according to claim 9, wherein said separating means includes a plurality of said capillaries, and wherein said apparatus further comprises a voltage applying means to apply a voltage for electrophoresis to each of said capillaries independently, and wherein said voltage applying means changes the voltage during electrophoresis based on the signal gained by said detecting means.

16. An apparatus according to claim 9, wherein said separating means includes a plurality of said capillaries, wherein said apparatus further comprises a voltage applying means to apply a voltage for electrophoresis to each of said capillaries independently, wherein said voltage applying means sets the migration voltage during a period when target DNA fragments are sampled to be smaller than the voltage for electrophoresis during a period when said DNA fragments are not sampled, and wherein said detecting means sets, in synchronism with the start of the period for sampling said DNA fragment, a sampling interval of said fluorescence and a time for gathering said fluorescence to be respectively greater than the sampling interval of said fluorescence and the time for gathering said fluorescence during a period when said DNA fragments are not sampled.

17. An apparatus for the separation and fractionation of differentially expressed gene fragments, the apparatus comprising:
   a capillary which is filled with a separation medium to separate by electrophoresis DNA fragments each being labeled with a fluorophore;
   a laser light source which generates a laser light to apply to the DNA fragments separated by electrophoresis in the capillary;
   a two-dimensional detector which detects fluorescence emitted from the fluorophore;
   transferring means including a sampling tube which is disposed such that an end of the sampling tube opposes an end of the capillary at a specified gap, separated DNA fragments eluted from the end of the capillary being transferred to an opening in the end of the sampling tube;
   means for forming a sheath flow of a buffer solution to carry the separated DNA fragments eluted from the end of the capillary to the opening in the end of the sampling tube;
   sampling means including sampling vessels to fractionate and sample the separated DNA fragments, according to their size, the separated DNA fragments being transferred by the sampling tube; and
   control means for controlling the sampling means based on the fluorescence detected by the two-dimensional detector;
   wherein the transferring means further includes
      means for forming droplets of the buffer solution containing the DNA fragments separated in the capillary, and
      transporting means for transporting the formed droplets to the sampling vessels by gas flow.

18. An apparatus for the separation and fractionation of differentially expressed gene fragments, the apparatus comprising:
   separating means including a capillary filled with a separation medium to separate DNA fragments by electrophoresis, the DNA fragments each being labeled with a fluorophore;
   detecting means for applying laser light to the DNA fragments separated in the capillary and for detecting fluorescence emitted from the fluorophore;
   transferring means including a sampling tube which is disposed such that a first end of the sampling tube opposes an end of the capillary at a specified gap, separated DNA fragments eluted from the end of the capillary being transferred to an opening in the first end of the sampling tube;
   means for forming a sheath flow of a buffer solution to carry the separated DNA fragments eluted from the end of the capillary to the opening in the first end of the sampling tube;
   sampling means including sampling vessels to fractionate and sample the separated DNA fragments, according to their size, the separated DNA fragments being transferred by the sampling tube; and
   a reservoir, having disposed therein a second end of the sampling tube, to contain buffer solution eluted from the second end of the sampling tube, a bottom of the reservoir having an aperture having a diameter enabling the sampling tube to be placed therethrough;
   a first tube to transport a washing fluid to the reservoir;
   a second tube to drain the buffer solution from the reservoir; and
   control means for controlling the sampling means based on a signal produced by the detecting means;
   wherein the second end of the sampling tube is placed through the aperture to transport the separated DNA fragments transferred by the sampling tube to the sampling vessels.

19. An apparatus for the separation and fractionation of differentially expressed gene fragments, the apparatus comprising:
   separating means including a capillary filled with a separation medium to separate DNA fragments by electrophoresis, the DNA fragments each being labeled with a fluorophore;
   detecting means for applying laser light to the DNA fragments separated in the capillary and for detecting fluorescence emitted from the fluorophore;
   transferring means including a sampling tube which is disposed such that an end of the sampling tube opposes an end of the capillary at a specified gap, separated DNA fragments eluted from the end of the capillary being transferred to an opening in the end of the sampling tube;
   means for forming a sheath flow of a buffer solution to carry the separated DNA fragments eluted from the end of the capillary to an opening in the end of the sampling tube;
   sampling means including sampling vessels to fractionate and sample the separated DNA fragments, according to their size, the separated DNA fragments being transferred by the sampling tube; and
   control means for controlling the sampling means based on a signal produced by the detecting means;
   wherein the laser light is applied to the capillary.

20. An apparatus for the separation and fractionation of differentially expressed gene fragments, the apparatus comprising:

separating means including a plurality of capillaries each filled with a separation medium to separate DNA fragments by electrophoresis, the DNA fragments each being labeled with a fluorophore;

voltage applying means for applying a voltage for electrophoresis to each of the capillaries independently;

detecting means for applying laser light to the DNA fragments separated in each of the capillaries and for detecting fluorescence emitted from the fluorophore;

transferring means including a sampling tube which is disposed such that an end of the sampling tube opposes an end of each of the capillaries at a specified gap, separated DNA fragments eluted from the end of each of the capillaries being transferred to an opening in the end of the sampling tube;

means for forming a sheath flow of a buffer solution to carry the separated DNA fragments eluted from the end of each of the capillaries to the opening in the end of the sampling tube;

sampling means including sampling vessels to fractionate and sample the separated DNA fragments, according to their size, the separated DNA fragments being transferred by the sampling tube; and control means for controlling the sampling means based on a signal produced by the detecting means;

wherein the voltage applying means changes the voltage during electrophoresis based on the signal produced by the detecting means.

21. An apparatus for the separation and fractionation of differentially expressed gene fragments, the apparatus comprising:

separating means including a capillary filled with a separation medium to separate DNA fragments by electrophoresis, the DNA fragments each being labeled with a fluorophore;

detecting means for applying laser light to the DNA fragments separated in the capillary and for detecting fluorescence emitted from the fluorophore;

transferring means including a sampling tube which is disposed such that an end of the sampling tube opposes an end of the capillary at a specified gap, separated DNA fragments eluted from the end of the capillary being transferred to an opening in the end of the sampling tube;

means for forming a sheath flow of a buffer solution to carry the separated DNA fragments eluted from the end of the capillary to the opening in the end of the sampling tube;

sampling means including sampling vessels to fractionate and sample the separated DNA fragments, according to their size, the separated DNA fragments being transferred by the sampling tube; and control means for controlling the sampling means based on a signal produced by the detecting means;

wherein the sampling tube has a length ranging from 5 cm to 15 cm and an inner diameter ranging from 50 $\mu$m to 100 $\mu$m; and wherein buffer solution flowing through the sampling tube has a flow rate about 10 mm/sec.

22. An apparatus for the separation and fractionation of differentially expressed gene fragments, the apparatus comprising:

a capillary which is filled with a separation medium to separate by electrophoresis DNA fragments each being labeled with a fluorophore;

a laser light source which generates a laser light to apply to the DNA fragments separated by electrophoresis in the capillary;

a two-dimensional detector which detects fluorescence emitted from the fluorophore;

a sampling tube which is disposed such that an end of the sampling tube opposes an end of the capillary at a specified gap, separated DNA fragments eluted from the end of the capillary being carried through a sheath flow of a buffer solution into the sampling tube to be transferred by the sampling tube;

a fraction collector which has sampling vessels to fractionate and sample the separated DNA fragments transferred by the sampling tube, according to their size; and a controller which controls a movement of the fraction collector based on the fluorescence detected by the two-dimensional detector;

wherein the sampling tube has an inner diameter greater than an outer diameter of the capillary.

23. An apparatus for the separation and fractionation of differentially expressed gene fragments, the apparatus comprising:

a capillary which is filled with a separation medium to separate by electrophoresis DNA fragments each being labeled with a fluorophore;

a laser light source which generates a laser light to apply to the DNA fragments separated by electrophoresis in the capillary;

a two-dimensional detector which detects fluorescence emitted from the fluorophore;

a sampling tube which is disposed such that an end of the sampling tube opposes an end of the capillary at a specified gap, separated DNA fragments eluted from the end of the capillary being carried through a sheath flow of a buffer solution into the sampling tube to be transferred by the sampling tube;

a fraction collector which has sampling vessels to fractionate and sample the separated DNA fragments transferred by the sampling tube, according to their size; and a controller which controls a movement of the fraction collector based on the fluorescence detected by the two-dimensional detector;

wherein the laser light is applied to the capillary.

24. An apparatus for the separation and fractionation of differentially expressed gene fragments, the apparatus comprising:

a capillary which is filled with a separation medium to separate by electrophoresis DNA fragments each being labeled with a fluorophore;

a laser light source which generates a laser light to apply to the DNA fragments separated by electrophoresis in the capillary;

a two-dimensional detector which detects fluorescence emitted from the fluorophore;

a sampling tube which is disposed such that a first end of the sampling tube opposes an end of the capillary at a specified gap, separated DNA fragments eluted from the end of the capillary being carried through a sheath flow of a buffer solution into an opening in the first end of the sampling tube to be transferred by the sampling tube;

a reservoir, having disposed therein a second end of the sampling tube, to contain buffer solution eluted from the second end of the sampling tube, a bottom of the reservoir having an aperture having a diameter enabling the sampling tube to be placed therethrough;

a first tube to transport a washing fluid to the reservoir;

a second tube to drain the buffer solution from the reservoir;

a fraction collector which has sampling vessels to fractionate and sample the separated DNA fragments transferred from an opening in the second end of the sampling tube, according to their size; and a controller which controls a movement of the fraction collector based on the fluorescence detected by the two-dimensional detector;

wherein the second end of the sampling tube is placed through the aperture to transport the separated DNA fragments transferred by the sampling tube to the sampling vessels.

25. An apparatus for the separation and fractionation of differentially expressed gene fragments, the apparatus comprising:

a capillary which is filled with a separation medium to separate by electrophoresis DNA fragments each being labeled with a fluorophore;

a laser light source which generates a laser light to apply to the DNA fragments separated by electrophoresis in the capillary;

a two-dimensional detector which detects fluorescence emitted from the fluorophore;

a sampling tube which is disposed such that a first end of the sampling tube opposes an end of the capillary at a specified gap, separated DNA fragments eluted from the end of the capillary being carried through a sheath flow of a buffer solution into an opening in the first end of the sampling tube to be transferred by the sampling tube;

a fraction collector which has sampling vessels to fractionate and sample the separated DNA fragments transferred from an opening in a second end of the sampling tube, according to their size;

a conical shaped member which has a hollow space through which the second end of the sampling tube passes; and a controller which controls a movement of the fraction collector based on the fluorescence detected by the two-dimensional detector;

wherein droplets of the buffer solution containing the separated DNA fragments are formed by flowing a gas into the hollow space; and wherein the formed droplets are transported to the sampling vessels by gas flow.

* * * * *